(12) United States Patent
Janowski et al.

(10) Patent No.: US 8,715,350 B2
(45) Date of Patent: May 6, 2014

(54) SYSTEMS AND METHODS FOR SECURING AN IMPLANT IN INTERVERTEBRAL SPACE

(75) Inventors: Brian P. Janowski, Marquette, MI (US); Jeffrey L. Trudeau, Marquette, MI (US); Michael R. Jackson, Hancock, MI (US); Russell M. Pietila, Hancock, MI (US)

(73) Assignee: Pioneer Surgical Technology, Inc., Marquette, MI (US)

(*) Notice: Subject to any disclaimer, the term of this patent is extended or adjusted under 35 U.S.C. 154(b) by 712 days.

(21) Appl. No.: 12/541,658

(22) Filed: Aug. 14, 2009

(65) Prior Publication Data

US 2010/0016974 A1 Jan. 21, 2010

Related U.S. Application Data

(63) Continuation-in-part of application No. 11/856,667, filed on Sep. 17, 2007, now Pat. No. 8,597,357.

(60) Provisional application No. 61/089,283, filed on Aug. 15, 2008, provisional application No. 60/825,865, filed on Sep. 15, 2006, provisional application No. 60/912,138, filed on Apr. 16, 2007.

(51) Int. Cl.
*A61F 2/44* (2006.01)

(52) U.S. Cl.
USPC ........................................... 623/17.14

(58) Field of Classification Search
USPC ......... 623/17.11–17.16; 606/70–71, 280–321
See application file for complete search history.

(56) References Cited

U.S. PATENT DOCUMENTS

| | | | |
|---|---|---|---|
| 4,636,217 A | 1/1987 | Ogilvie et al. | |
| 4,759,769 A | 7/1988 | Hedman et al. | |
| 5,108,399 A * | 4/1992 | Eitenmuller et al. | ........... 606/77 |
| 5,123,926 A | 6/1992 | Pisharodi | |
| 5,314,477 A | 5/1994 | Mamay | |
| 5,425,773 A | 6/1995 | Boyd et al. | |

(Continued)

FOREIGN PATENT DOCUMENTS

| | | |
|---|---|---|
| CA | 2 548 780 | 7/2005 |
| DE | 296 12 269 U1 | 10/1996 |

(Continued)

OTHER PUBLICATIONS

Patent Cooperation Treaty, International Search Report from corresponding International Patent Application No. PCT/US2007/078679, Apr. 23, 2008, 1 p.

(Continued)

*Primary Examiner* — Matthew Lawson
(74) *Attorney, Agent, or Firm* — Fitch, Even, Tabin & Flannery LLP

(57) ABSTRACT

An intervertebral disc implant with upper and lower bearing members with an articulation interface between the members for providing relative motion therebetween. In one form, a securing member with an elongate shaft and a bone-engaging member on the shaft is disposed on one of the bearing members. The bone-engaging member is deployable into a bone-engaging position via rotational displacement of the shaft. In another form, a bone-engaging member is deployable via an actuator inserted into the implant body. In another form, the securing member secures an intervertebral implant in intervertebral space via deformation of the securing member causing a bone-engaging member of the securing member to be deployed into contact with an adjacent vertebra.

22 Claims, 25 Drawing Sheets

(56) References Cited

U.S. PATENT DOCUMENTS

| | | |
|---|---|---|
| 5,507,816 A | 4/1996 | Bullivant |
| 5,676,701 A | 10/1997 | Yuan |
| 5,800,547 A | 9/1998 | Schaefer et al. |
| 5,888,226 A | 3/1999 | Rogozinski |
| 6,039,763 A | 3/2000 | Shelokov |
| 6,146,421 A | 11/2000 | Gordon et al. |
| 6,210,442 B1 | 4/2001 | Wing et al. |
| 6,371,987 B1 * | 4/2002 | Weiland et al. ............ 623/17.11 |
| 6,527,803 B1 * | 3/2003 | Crozet et al. ............... 623/17.11 |
| 6,540,785 B1 | 4/2003 | Gill et al. |
| 6,610,093 B1 | 8/2003 | Pisharodi |
| 6,767,367 B1 | 7/2004 | Michelson |
| 6,770,096 B2 | 8/2004 | Bolger et al. |
| 6,923,830 B2 | 8/2005 | Michelson |
| 6,926,737 B2 | 8/2005 | Jackson |
| 6,936,071 B1 | 8/2005 | Mamay et al. |
| 6,981,975 B2 | 1/2006 | Michelson |
| 7,056,341 B2 | 6/2006 | Crozet |
| 7,074,240 B2 | 7/2006 | Pisharodi |
| 7,662,182 B2 | 2/2010 | Zubok et al. |
| 7,682,397 B2 | 3/2010 | Berry et al. |
| 7,794,465 B2 | 9/2010 | Marik et al. |
| 7,819,920 B2 | 10/2010 | Assaker |
| 7,909,859 B2 | 3/2011 | Mosca et al. |
| 8,038,678 B2 | 10/2011 | Schmieding et al. |
| 8,303,660 B1 * | 11/2012 | Abdou ....................... 623/17.14 |
| 2002/0035400 A1 | 3/2002 | Bryan et al. |
| 2002/0165613 A1 | 11/2002 | Lin et al. |
| 2003/0149484 A1 | 8/2003 | Michelson |
| 2004/0006394 A1 | 1/2004 | Lipman et al. |
| 2004/0044410 A1 | 3/2004 | Ferree et al. |
| 2004/0093082 A1 | 5/2004 | Ferree |
| 2004/0193272 A1 | 9/2004 | Zubok et al. |
| 2004/0243240 A1 | 12/2004 | Beaurain et al. |
| 2005/0038515 A1 | 2/2005 | Kunzler |
| 2005/0049590 A1 * | 3/2005 | Alleyne et al. .................. 606/61 |
| 2005/0071010 A1 | 3/2005 | Crozet |
| 2005/0080488 A1 | 4/2005 | Schultz |
| 2005/0107881 A1 | 5/2005 | Alleyne et al. |
| 2005/0273166 A1 | 12/2005 | Sweeney |
| 2006/0004453 A1 | 1/2006 | Bartish |
| 2006/0020341 A1 | 1/2006 | Schneid et al. |
| 2006/0085076 A1 | 4/2006 | Krishna et al. |
| 2006/0095136 A1 | 5/2006 | McLuen |
| 2006/0116767 A1 | 6/2006 | Magerl et al. |
| 2006/0136062 A1 | 6/2006 | DiNello et al. |
| 2006/0178744 A1 | 8/2006 | de Villiers et al. |
| 2006/0178745 A1 | 8/2006 | Bartish, Jr. et al. |
| 2006/0195191 A1 | 8/2006 | Sweeney, II et al. |
| 2006/0212122 A1 | 9/2006 | Perera |
| 2006/0293752 A1 | 12/2006 | Moumene et al. |
| 2007/0055376 A1 | 3/2007 | Michelson |
| 2007/0100455 A1 | 5/2007 | Parsons |
| 2007/0270961 A1 * | 11/2007 | Ferguson ................... 623/17.11 |
| 2007/0288005 A1 * | 12/2007 | Arnin et al. ..................... 606/61 |
| 2008/0103598 A1 | 5/2008 | Trudeau et al. |
| 2009/0240333 A1 | 9/2009 | Trudeau et al. |
| 2010/0280619 A1 | 11/2010 | Yuan et al. |

FOREIGN PATENT DOCUMENTS

| | | |
|---|---|---|
| DE | 198 16 832 C1 | 1/2000 |
| WO | 0049977 | 8/2000 |
| WO | WO2006016384 | 2/2006 |

OTHER PUBLICATIONS

Patent Cooperation Treaty, International Search Report from corresponding International Patent Application No. PCT/US2009/042882, Jun. 22, 2009, 2 pp.

European Patent Office, Supplementary European Search Report from corresponding International Patent Application No. PCT/US2007/078679, Jan. 28, 2013, 10 pp.

* cited by examiner

US 8,715,350 B2

SYSTEMS AND METHODS FOR SECURING AN IMPLANT IN INTERVERTEBRAL SPACE

RELATED APPLICATIONS

This application is a continuation-in-part of U.S. patent application Ser. No. 11/856,667, filed Sep. 17, 2007 now U.S. Pat. No. 8,598,357, which claims the benefit of U.S. Provisional Application No. 60/825,865, filed Sep. 15, 2006 and U.S. Provisional Application No. 60/912,138, filed Apr. 16, 2007. This application also claims the benefit of U.S. Provisional Patent Application No. 61/089,283, filed Aug. 15, 2008. U.S. patent application Ser. No. 11/856,667 and U.S. Provisional Application 61/089,283 are both incorporated herein by reference in their entirety.

FIELD OF THE INVENTION

The invention relates to systems and methods for securing an implant within a joint and, more particularly, to systems and methods for securing an implant in the intervertebral space.

BACKGROUND OF THE INVENTION

Joint degeneration is a common problem that can occur in a variety of joints throughout the human body. The condition typically is more prevalent as the skeletal system ages and is often treated with medications and/or physical therapy. These conservative treatments sometimes meet only limited success. If unsuccessful, the patient typically will continue to experience ongoing pain and limited mobility.

Often the treatment progression leads to a total joint replacement. These replacements have been performed for years in joints such as the hip and the knee. The replacement devices usually comprise some form of a metallic structural component or endplate with an intermediate polyethylene core. It is not unusual for replacements such as these to give 15-20 years of service before requiring some degree of revision.

In the spine, the surgical treatment of choice has been fusion for the treatment of intervertebral disc degeneration. The spinal intervertebral disc is arguably the most important joint in the spine and is situated between the vertebral bodies. The spinal disc is comprised of a tough outer ring called the annulus, and a jelly-like filling called the nucleus. The belief has been that removing the diseased spinal disc(s) and fusing between affected levels will not make a significant difference in the overall mobility of the spine. However, spinal fusion has proved to cause an increase in degeneration at other vertebral levels that must compensate for the loss of motion at the fused level commonly causing the patient to relapse into more pain and limited mobility.

Recently, there has been a focus on the use of "motion preservation" implants over implants that promote spinal fusion. These motion preserving implants, in the form of joint replacements in the spine, hope to alleviate many of the problems associated with fusion devices in the spine. Intervertebral disc replacement devices are seen today typically comprising a pair of biocompatible metal plates with a polymer or elastomeric core, or a metal plate articulating on a metal plate.

Metal on metal implants have a history of failure in long term use, however, precision machining has spawned a reemergence of implants using these materials since it is believed that this change in manufacturing greatly improves the wear. Regardless, the metal implants are radiopaque and continue to frustrate surgeons due to the difficulty in imaging the affected area. Other implants, such as those using a polymer or elastomeric core between metallic plates suffer from the same radiopaque frustrations due to the metal components in addition to the added complexities of design due to the necessity of utilizing a multitude of materials for a single implant.

The prior art discloses a laundry list of biocompatible materials including metals, ceramics, and polymers, that can be used for the manufacture of these implants, yet historically many of these materials have failed when interfaced together and tested in an articulating joint. There is in particular an extensive history of failure when polymers articulate against polymers in weight bearing artificial joints. Due to this failure history, polymer combinations have naturally been excluded as an acceptable self-articulating material combination for use in weight bearing joint replacements.

PEEK (poly-ether-ether-ketone), for example, has been suggested as an appropriate material of manufacture for use in implant devices due in large part to its strength, radiolucent nature, and biocompatibility. This is particularly true in structural implants having no articulating component. PEEK on PEEK has been suggested for use in low wear non-weight bearing joints such as in finger joints. However, the prior art has been careful not to suggest self-articulating PEEK on PEEK as a suitable material combination in weight bearing joint replacement devices due to the failure history of biocompatible polymers articulating against themselves.

One important consideration in the design of an implant is ensuring that the implant remains at the implant site, and does not migrate. Migration of the implant away from the intended implant site can cause dangerous and even fatal complications. In the case of an intervertebral implant, the close proximity of vital blood vessels, nerves, the spinal cord, and other vital tissues makes securing the implant in place a vital concern. Many different ways to secure the implant to the adjacent bone of the joint have been proposed, including implementing protrusions or spikes, keels, screws, surface roughening, and bone-growth inducing coatings.

In one known form disclosed in Published U.S. Patent Application 2007/0270961, a spinal implant is provided with deployable and retractable barbs for securing the implant to a vertebra. In one embodiment, the barbs 130 have arcuate bodies having sharpened tips for protruding into the vertebral bone. The barbs 130 are disposed within recesses 120 in the implant body 110 and rotatably mounted on pins 140. The pins 140 are disposed transversely to channel 160, such that the barb rotates about the pin along the longitudinal axis of the channel. The barbs 130 are deployed via interaction with a rod 150 that is inserted into the channel 160 of the implant body 110. The rod 150 has a sloped end for engaging the barbs 130 and causing them to rotate upwards about the pins 140 and into engagement with the bone.

In another form according to U.S. Patent Application 2007/0270961 shown in FIG. 5A-5D of that application, the deployable barbs take the form of conical spikes 530 configured to be deployed into the adjacent vertebra for securing the implant thereto. The spikes 530 have lower edges 538 which engage with the tapered tip 552 of the rod 550, which propels the spikes through apertures 520 in the implant body 500. The implant is also supplied with a lock mechanism 548 in the form of annular washers that prevent the barb 530 from exiting the implant body 510.

One embodiment shown in FIG. 6 of U.S. Patent Application 2007/0270961 is described as having a nucleus portion 650 that may comprise a ball and trough arrangement to permit translational and rotational motion therebetween.

However, the figures of the application do not disclose such a nucleus portion, and it is believed that the implants shown and described therein would be unable to incorporate such a configuration. Specifically, the implant bodies do not have sufficient material thickness to incorporate at least a trough portion for a ball and trough configuration.

In addition, in the configurations of the embodiments shown in 1A-4D of U.S. Patent Application 2007/0270961, the implant would be drawn further into the intervertebral space by the deployment of the barbs due to their shape and their axis of rotation about the pins. This pulling effect is believed to be counteracted by the protrusions 172 disposed on the end of the implant, such that an inner surface of the protrusions can bias against a surface of the adjacent vertebra, thereby preventing the implant from being pulled further into the intervertebral space. However, implants that have protrusions that extend outside of the intervertebral space are less preferred. For example, a cervical implant that protrudes from the intervertebral space between adjacent vertebrae may come into contact with the trachea, which can cause pain or difficulty in swallowing.

SUMMARY OF THE INVENTION

Two piece articulating PEEK on PEEK intervertebral implants have been presented in earlier applications by the same inventor. These implants perform exceptionally well for replacement of the spinal nucleus. However, many indications require implants of this nature to also comprise improved restraining features particularly in weight bearing applications.

For example, there is a need for a simplified radiolucent artificial disc device, with excellent wear characteristics and features that will secure the device to the vertebral endplates or otherwise restrain it between the vertebral bodies. An artificial disc such as this would be particularly useful as a lumbar disc replacement, and even more so as a cervical disc replacement. The cervical disc is much smaller than the lumbar disc as is the space the cervical disc occupies. For at least this reason, a simplified design utilizing fewer parts is beneficial.

In some forms, the securing member is associated with the implant to be inserted into the intervertebral space therewith. After the disc and securing member are inserted in the intervertebral space, the securing member can be deployed into the adjacent vertebral bodies from the disc implant. In one form, the insertion tool is used to engage the securing member with the intervertebral bodies. In another form, the securing member is actuated directly to engage the securing member with the vertebral bodies.

The securing members generally possess structure which allow for dynamic fixation of the implant. Instead of relying solely on subsidence or boney ingrowth of the bone around the features of the implant, the securing members actively engage the bone for immediate and reliable fixation of the implant to the vertebrae. In one embodiment, a rotatable shaft with at least one bone engaging body is disposed on the implant for securing the implant within the intervertebral space. In an undeployed position, the bone engaging body is disposed within the implant body. When the shaft is rotated, the bone engaging body is deployed into the vertebra and thereby fixes the implant to the vertebra to prevent migration of the implant.

In some forms, the securing member is disposed on the upper and lower surfaces of the upper and lower faces of the implant. However, in other forms, the securing member may be completely submerged within the body of the implant such that the upper and lower surfaces with the implant are relatively smooth or flat. When the securing member is securely submerged within the implant, the upper and lower vertebrae need not be prepared prior to the insertion of the implant, thereby simplifying the implantation procedure.

In another form, an implant according to the present invention may be provided with upper and lower bearing members having respective bodies and outer bearing surfaces. An articulation interface disposed between the upper and lower bearing members allows for relative movement therebetween. A securing member is disposed on one of the bearing members and has an elongate shaft portion and a bone-engaging member disposed on the shaft portion. The bone-engaging member is movable from an undeployed position, wherein the bone-engaging member is positioned out of engagement with an adjacent bone, and a deployed position, wherein the bone-engaging member is positioned in engagement with the adjacent bone via rotational displacement of the shaft portion. In some forms, the securing member is entirely disposed within the body of the bearing member when in an undeployed position.

In other forms, the securing member may include at least one bone engaging body disposed on the implant which is deployed into the vertebrae by the insertion of an elongate member into the implant body. The bone engaging body is disposed on the implant such that insertion of the elongate member causes the bone engaging body to be deployed from its initial position to a bone engaging position. Once the elongate member is inserted into the implant body, the bone engaging body is fully deployed and the elongate body is left within the implant to hold the bone engaging body in the deployed position.

The securing member in some forms includes an elongate shaft portion disposed within a channel of the bearing member and may have a plurality of bone engaging members. The bone engaging members may be lobe members having bodies orientated generally transversely to the elongate shaft portion. The lobe members may have a sharpened portion for easing insertion of the lobe member into the vertebral bone by either cutting or piercing the bone. In other forms, the lobe members may be sized and configured for engaging with prepared surfaces of the vertebra, wherein the surfaces are prepared prior to the insertion of the implant. The vertebra may be prepared using a cutting tool to form a securing member receiving portion by removing bone at the implant site. The bone may be prepared by cutting grooves or channels sized and configured to receive the securing member.

The securing member may be connected to the body of the bearing member via a retainer member for connecting the securing member to the bearing member body. In one form, the retainer securing member has opposing arms spaced from each other for receiving the elongate shaft member between the opposing arms by a friction fit.

The upper and lower bearing members may be sized and configured to fit entirely between inner surfaces of adjacent vertebrae when the deployable securing member is in an undeployed configuration. This configuration eases insertion of the implant, because the vertebrae need not be prepared prior to insertion. Moreover, in a preferred form, the implant fits entirely within the footprint of the intervertebral disc space such that the implant does not interfere with adjacent blood vessels, nerves, tissues, digestive or respiratory tracts and the like.

In another form according to the present invention, an intervertebral disc implant has a deployable securing member disposed on the implant body with a projection of the deployable securing member movably connected to the body having a head portion with an edge for engaging a bone, an actuation portion of the securing member having an actuator engagement portion thereon. The projection is deployable between an undeployed position, wherein the projection is remote from an adjacent vertebra, to a deployed position, wherein the projection is engaged with the adjacent vertebra through the interaction of the actuator with the projection when the actuator is inserted along an insertion axis into the body. The head portion of the deployable securing member is oriented in a generally transverse orientation with respect to the insertion axis when the securing member is in a deployed position.

The implant body has an outer bone engaging surface for non-invasive contact with an inner surface of the adjacent vertebra and a securing member mating portion of the implant body for mating with the securing member which protrudes outwardly beyond the bone engaging surface. The securing member mating portion comprises an elongate opening for receiving the projection and allowing the projection to travel from the undeployed position, wherein the projection is disposed within the opening, to a deployed position, wherein the projection protrudes from the opening and is brought into engagement with the adjacent vertebra. The implant body may be part of a unitary implant, such as a spacer implant, or the implant body may be one member of a multiple-part implant, such as one of upper and lower bearing members. In a multi-part implant, the upper and lower bearing members may be provided with upper and lower inner arcuate bearing surfaces that slidingly engage one another. The sliding interface between the upper and lower bearing members between the upper and lower inner arcuate bearing surfaces allows the bearing members to articulate with respect to one another. In one form, the upper and lower inner arcuate bearing surfaces are sized and configured to allow the upper and lower bearing members to rotate with respect to one another over a range of approximately 13.7-22.5 degrees in flexion and 13.8-30 degrees in extension, depending on implant size.

In one form, the edge of the projection is deployed rostrally or caudally into engagement with the adjacent vertebra without substantial translation in another direction. For example, the projection may be a spade-like lobe that is driven straight up into the vertebral bone when it is actuated by an actuator. In other forms, the projection is connected to a pivot shaft connected to the implant body and oriented generally parallel to the insertion axis such that the projection pivots along with the shaft in a direction transverse to the insertion axis during deployment of the projection. Preferably, the projection and pivot shaft rotate about a pivot shaft axis parallel to the insertion axis during deployment of the projection.

In yet another form, the securing member may take the form of a bendable elongate member that may be inserted into a securing member receiving portion of the upper or lower face of the implant. The bendable elongate member is inserted into the securing member receiving portion which causes the bendable elongate member to flex or bend causing a projection to protrude into the adjacent vertebrae thereby fixing the implant to the vertebrae. The bendable elongate member may include preformed protrusions that are deployed upon compression of the elongate member.

The implant preferably includes an implant body having a securing member receiving portion. A bendable securing member for being inserted into the securing member receiving portion is provided to secure the implant to the vertebra. The bendable securing member is inserted into an opening of the securing member receiving portion to deploy a bone engaging member of the bendable securing member. The bone engaging member is movable from an undeployed orientation, wherein the bone engaging member is remote from an adjacent vertebra, and a deployed orientation, wherein the bone engaging member is brought into contact with the adjacent vertebra for securing the implant body to the adjacent vertebra. In some forms, the bone engaging member is deployed through the plastic deformation of the securing member upon insertion of the securing member into the opening of the securing member receiving portion. An abutment surface of the implant body is provided for engaging with the securing member to facilitate deformation of the securing member by compression of the securing member against the abutment surface. The bone engaging member may be a barb member disposed on the bendable securing member. In a preferred form, the barb member is disposed flush to an outer surface of the securing member prior to deployment of the barb. The bone engaging member may have a structurally weakened portion to promote plastic deformation thereof at a predetermined position to deploy the bone engaging member at a desired location. The bendable member preferably comprises a plurality of bone engaging members.

In some forms, the securing member receiving portion has an opening on an outer facing surface of the implant body which permits the bone engaging member to pass through the opening and engage the adjacent vertebra. The bone engaging member is preferably predisposed to bending at locations thereon that correspond to an opening or openings in the outer facing surface of the implant body.

BRIEF DESCRIPTION OF THE DRAWINGS

To understand the present invention, it will now be described by way of example, with reference to the accompanying drawings in which.

DETAILED DESCRIPTION OF PREFERRED EMBODIMENTS

In a preferred embodiment, such as illustrated in FIGS. 1-21, an artificial disc device comprises an upper bearing member and lower bearing member. In FIGS. 1-8, only the upper bearing member 8 is shown, although an implant according to the present invention preferably includes both upper and lower bearing members. The lower bearing member is preferably similar in structure to those illustrated in FIGS. 9-17. An implant according to the present invention includes one or more restraint portion(s) or structure located on one or both of the bearing members to help keep the bearing members from becoming dislodged or migrating across the inner surface or endplate of the vertebrae (not shown) after insertion. The restraint portion may take the form of a deployable securing member 6, which is movable from an undeployed configuration, wherein the restraining portion is positioned remotely from the adjacent bone surface and a deployed configuration, wherein the restraining portion is positioned in contact with the adjacent bone for affixing the implant thereto. Described in this application are various securing members that can be used on the endplate facing surfaces of a vertebra to restrain an implant.

Figure 1:
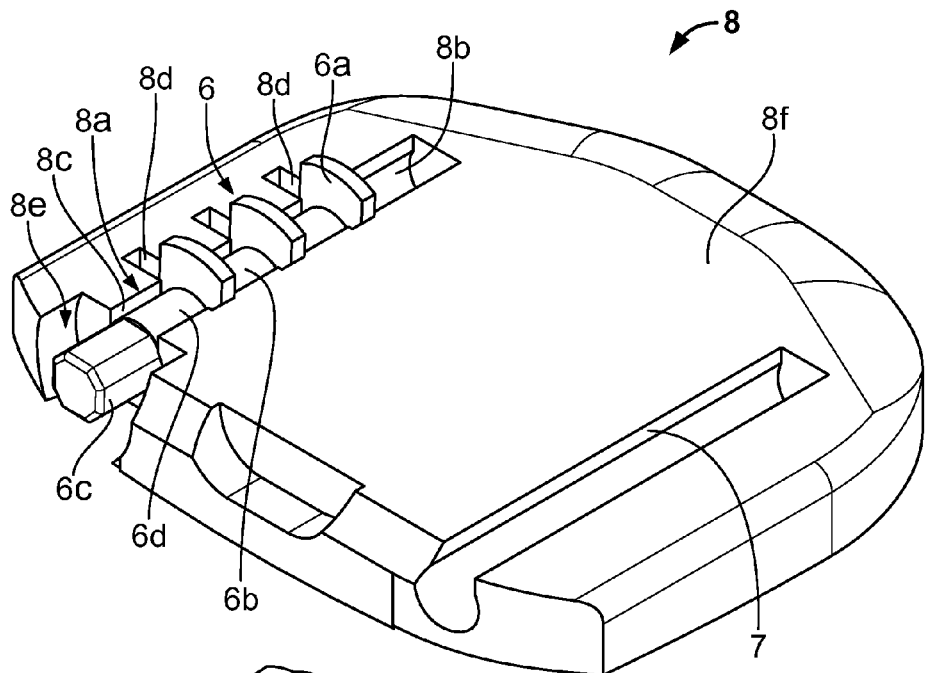
FIG. 1 is a anterolateral perspective view of a bearing member of an intervertebral implant according to the present invention illustrating a deployable securing member in a bone engaging orientation.

In the form shown in FIGS. 1-8, an upper bearing member 8 is shown with a single securing member 6. The elongate groove 7 formed in the outer bearing surface 8f of the upper bearing member 8 shown on the right hand side in FIG. 1 is preferably replaced by a restraint portion similar to securing member 6 to increase gripping engagement with the vertebra. Thus, the securing member 6 shown serves as an example according to the present invention, and may be located on other portions of an implant, alone or in combination with other securing members 6.

The securing member 6 in the present form has restraint portions in the form of deployable bone engaging members 6a. The bone engaging members 6a are disposed on an elongate shaft 6b housed within the body of the bearing member 8. In a preferred orientation, the securing member 6 is secured within a recess 8b of the body of the bearing member 8 by a securing member receiving portion 8a in the form of a snap joint. A neck portion 6d of the elongate shaft 6b is held by opposing inner surfaces 8c of the receiving portion 8a via an interference or friction fit. In this regard, the preferred PEEK material from which the bearing members including the receiving portion 8a thereof are formed provides the receiving portion 8a with sufficient strength and resiliency to provide a secure friction fit with the shaft portions 6b snap-fit therebetween while allowing for the shaft portions 6b to be rotated to secure the bearing member 8 to the corresponding adjacent vertebrae. This configuration is advantageous, because it requires no additional fasteners, pins, or supports, thereby reducing parts and increasing reliability and safety of the implant.

The elongate shaft 6b is preferably configured with a profile suitable for rotation. The elongate shaft is 6b provided with a drive head 6c operable to mate with an actuator, such as a driver, operable to deploy the restraint portions via rotation of the elongate shaft 6b. The securing member receiving portion 8a includes an actuator receiving portion 8e for receiving the actuator therein. In the form illustrated in FIGS. 1-8, the actuator receiving portion 8e provides clearance for the driver to grasp the drive head 6c, and keeps the drive head 6c from protruding outside of the footprint of the implant body. This feature increases the safety and comfort of the implant over other known implants, because implants with projections that extend outside of the implant body and especially outside of the intervertebral space can interfere with adjacent vital tissues, nerves, blood vessels, and the digestive and respiratory tracts.

The bone engaging members 6a take the form of lobe members that may be deployed into engagement with the endplate of the vertebrae upon rotation of a drive head 6c of the elongate shaft 6b using the proper instrument. The lobe members 6a have bodies oriented generally transversely to a longitudinal axis of the elongate shaft 6b. In this orientation, the lobe members 6a keep the implant from migrating, particularly in the direction along the longitudinal axis. The lobe members 6a may include a sharpened edge for easing the deployment of the lobe members 6a into the adjacent bone. The lobe members 6a may include apertures or slots to encourage bone growth therethrough. In addition, the lobe members 6a may take a variety of sizes and shapes. Additional examples of securing members may be found in U.S. patent application Ser. No. 11/856,667, filed Sep. 17, 2007, which is incorporated herein in its entirety. Further, although the securing member 6 is shown having three lobe members 6a, different numbers of bone engaging members may be implemented. The securing member may be manufactured from an array of biocompatible materials, including, but not limited to polymers such as PEEK or metals such as titanium or stainless steel alloys, although radiolucent materials are preferred.

Figure 2:
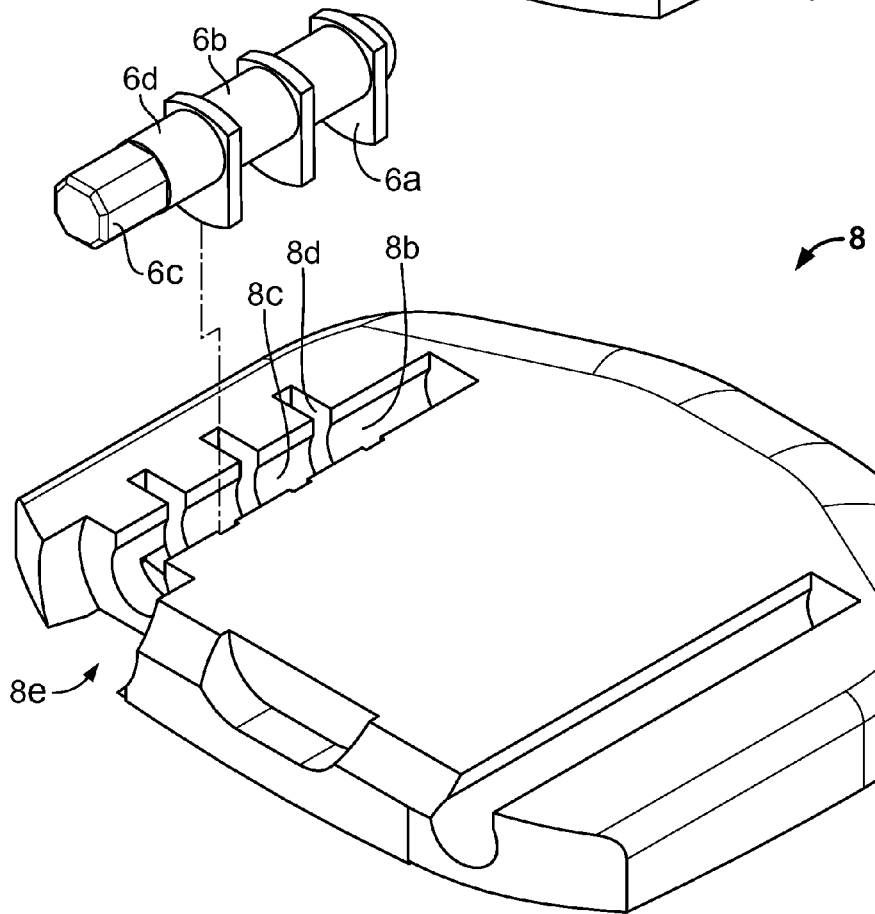
FIG. 2 is an exploded anterolateral perspective view of the bearing member of FIG. 1.
Figure 3:
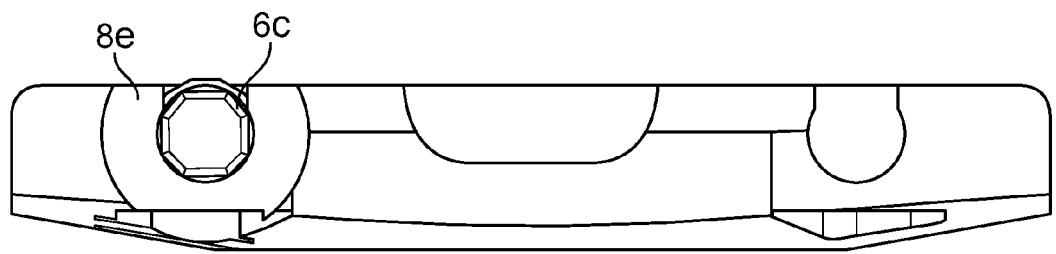
FIG. 3 is an anterior view of the bearing member of FIG. 1 illustrating the deployable securing member in an undeployed configuration, wherein the securing member is completely submerged within the bearing member so as to not protrude above the upper bearing surface.
Figure 4:
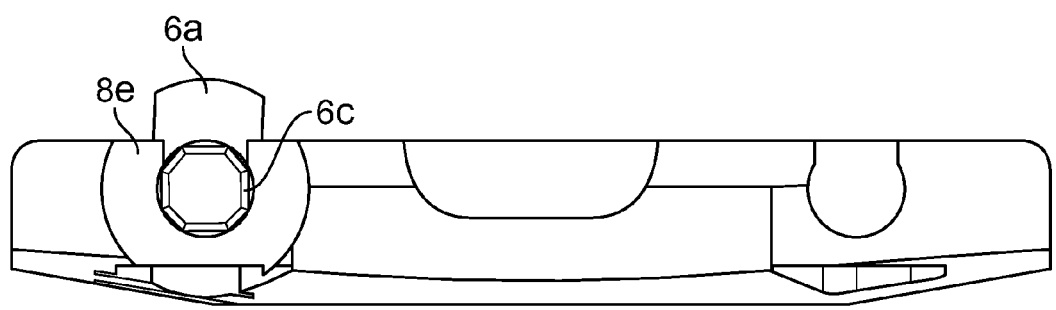
FIG. 4 is an anterior view of the bearing member of FIG. 3 illustrating the deployable securing member in a deployed configuration, wherein the securing member protrudes above the upper bearing surface for engagement with a bone.
Figure 5:
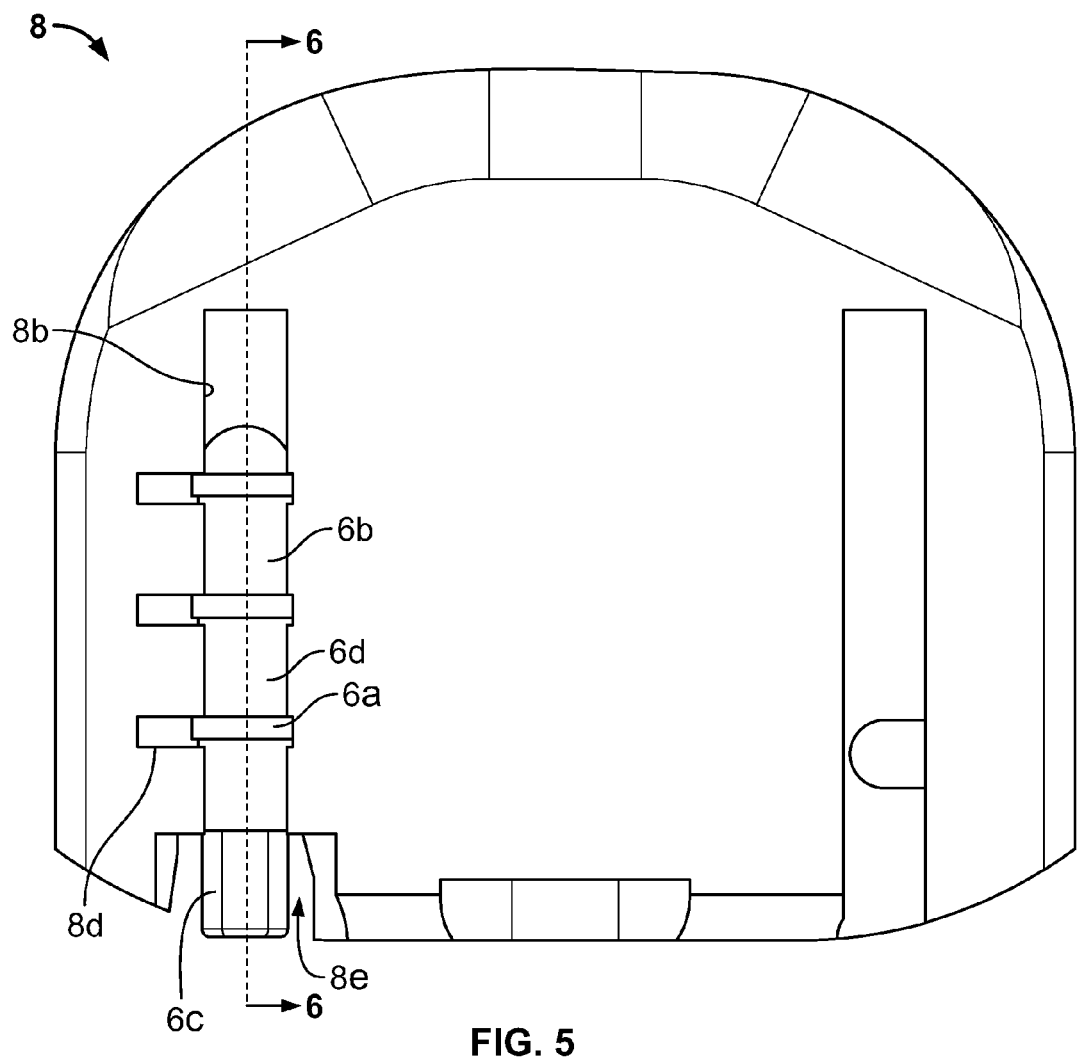
FIG. 5 is a plan view of the bearing member of FIG. 1 illustrating the deployable securing member in a deployed configuration.
Figure 6:
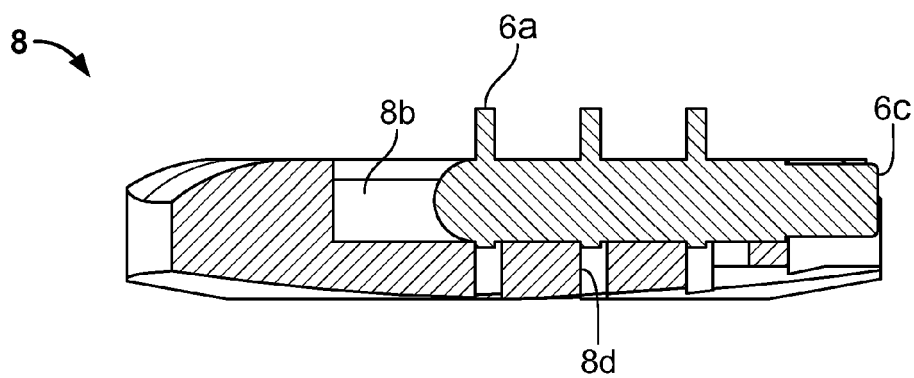
FIG. 6 is a lateral cross-sectional side view of the bearing member of FIG. 1, illustrating the deployable securing member receiving portion, and the securing member in a deployed configuration.
Figure 7:
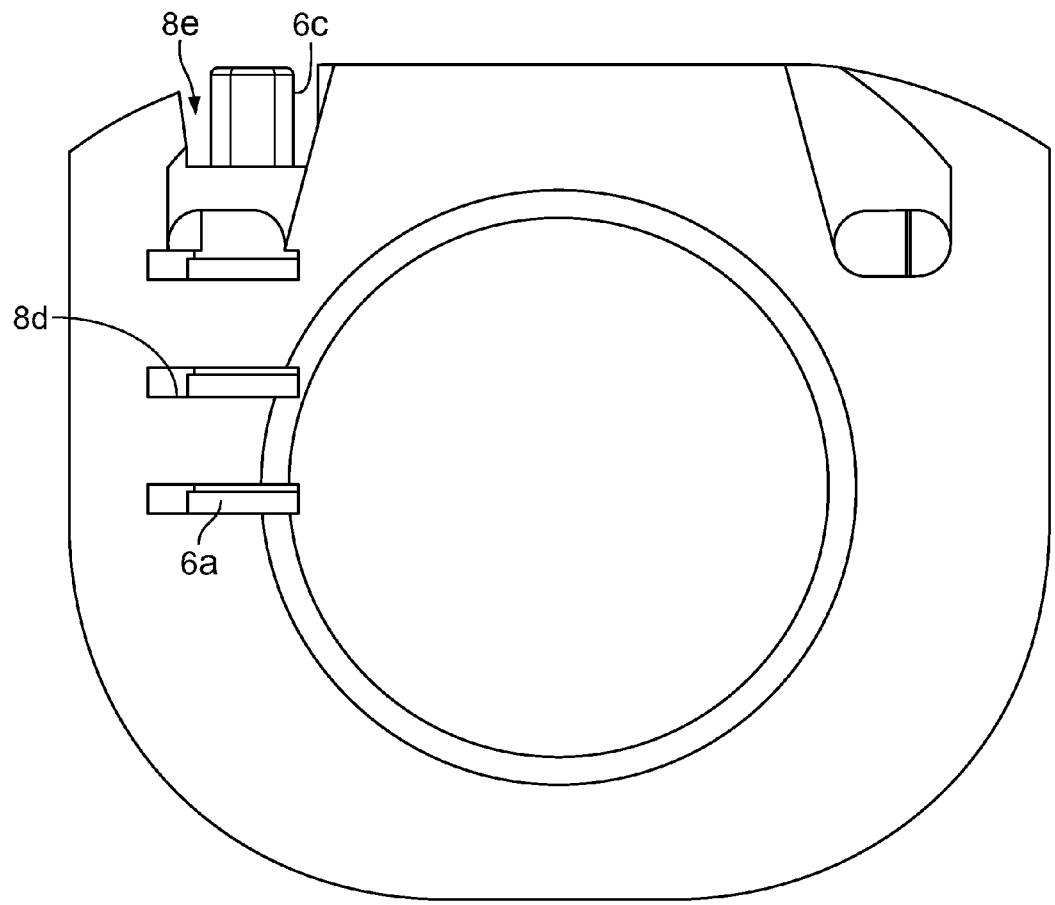
FIG. 7 is a bottom view of the bearing member of FIG. 1, illustrating the concave articulation surface disposed on an inner surface of the bearing member.
Figure 8:
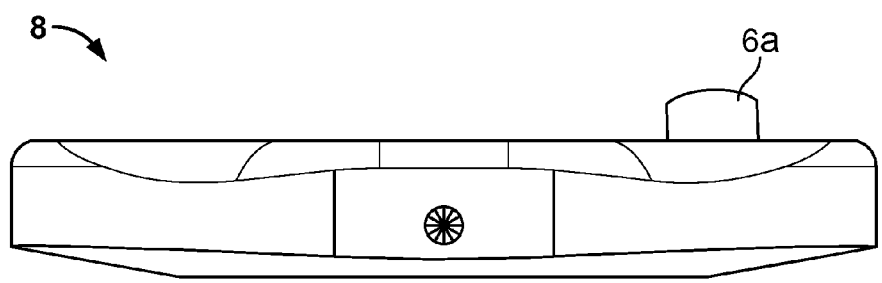
FIG. 8 is a posterior view of the bearing member of FIG. 1, illustrating the deployable securing member in a deployed configuration and a centrally located marking member disposed in the bearing member body.

More specifically, the securing member 6 includes several lobe members 6a spaced along the length thereof. Initially, in an undeployed configuration, the securing member 6 is oriented with the lobe members 6a oriented downwards or towards the interior of the implant, as shown in FIGS. 2 and 3, for insertion of the implant into the intervertebral space. The lobe members 6a are received in the restraint portion recesses 8d formed in the upper surface 8f of the upper bearing member 8. Rotating the shaft 6b 180 degrees via a driver from its undeployed insertion orientation to its deployed bone-engaging orientation shifts the lobes 6a either into recesses cut into the vertebral body, if the vertebra has been prepared prior to insertion of the implant, or directly into the adjacent bone if the vertebra has not been prepared. In this manner, the artificial disc device may be secured in the intervertebral space against extrusion out therefrom during articulation of upper and lower bearing members relative to each other as the upper and lower vertebrae shift via an arcuate bearing interface formed between the members (see e.g., FIG. 10).

Once the disc device is inserted, the restraining portions may be deployed into the endplate to secure the artificial disc device in the desired location between the vertebrae. In the embodiment shown in FIGS. 1-8, the securing member is completely submerged within the body of the implant, such that the implant may be inserted without need for any preparation of the vertebral bodies prior to insertion. Thus, this embodiment is advantageous for ease of insertion and for reducing trauma to the implant site. However, in some cases it may be preferable to implement an implant having a securing member that protrudes outside of the bone engaging surface of the bearing member.

In the embodiments shown in FIGS. 9-21, the surgeon may be required to prepare the vertebral body to accept restraint portions that are intended to become integrated into the bone. In most cases, this preparation involves removing bone and creating restraint access portions typically in the form of a recess, channel, slot or profile similar to the restraint feature. Obviously, the size of the restraint portion will affect the size of the restraint access portion. Therefore, it is beneficial that restraint portions that interfere with the bone are suitably sized to prevent an oversized restraint access that compromises the vertebrae and risks vertebrae fracture. It is preferable that both the restraint access and restraint portion have radiused edges to reduce stress concentrations in the vertebral body.

The deployable securing member 6, including the deployable bone engaging members 6a may take on different geometries and orientations to improve performance of the securing member 6. For example, the lobe members 6a may include serrations, divots, or recesses to promote boney ingrowth. The serrations may also help to cut the bone when the securing member 6 is rotated. In addition, the lobe members 6a may be cupped or slanted to further promote anchoring of the implant to the vertebrae. Further, the lobe members 6a may have an outside contour, such that shape or size of the lobe members 6a varies from one end of the shaft 6b to the other. The contour may match the profile of the endplates to take advantage of the softer bone in the center of the vertebrae as opposed to the harder-denser bone at the periphery of the vertebrae. Further, the shafts 6b may have any number of lobe members 6a. In a preferred embodiment, each shaft 6b may have between three and five lobe members 6a. Larger implants may have five members per shaft 6b, while smaller implants may have only three. The shafts 6b are preferably made from titanium or stainless steel, and may be coated with a bone-growth promoting substance, such as hydroxyapatite, tricalcium phosphates, or calcium phosphates.

In other forms, the shaft(s) 6b on the upper or lower bearing members may be disposed at converging or diverging angles. This orientation prevents migration of the implant not only in an anterior/posterior direction, but also substantially in the lateral direction as well.

The securing members 6 of the embodiment described in FIGS. 1-8 may provide tactile feedback regarding the position of the securing member 6 to the surgeon as the securing member 6 is deployed. Because the bone is relatively soft compared to the projections 6a being deployed into the bone, the bone provides little resistance to the projections 6a as they are deployed into the bone. Therefore, it is helpful to provide the surgeon with tactile feedback so that he does not over- or under-deploy the projections, causing the implant to be improperly affixed to the bone. In addition, the securing member may be provided with positive retraction blocking structure. Because the vertebral bone provides only a limited amount of resistance to the deployable projections, the projections may be prone to retract, derotate, or otherwise begin to return to their original undeployed position over time. Thus, retraction blocking structures may be provided on the disc implant to avoid this condition.

In another form in accordance with the present invention, an intervertebral implant 102 with a deployable securing member 106 is shown in FIGS. 9-13. Generally, the implant has upper and lower bearing members 108, 110, each having a plurality of deployable securing members 106 disposed on the outer bearing surfaces 108f, 110a. Although the current embodiment is shown with a single securing member 106 with a plurality of restraining portions disposed on the upper bearing member 108, a preferred embodiment has at least one securing member 106 on each bearing member 108, 110.

The securing member 106 of FIGS. 9-13 includes a plurality of restraining portions in the form of deployable plate members 106a. Each deployable plate member 106a has a head portion 106b and two opposing legs 106c. The head portion 106b is preferably provided with a blade or sharpened tip 106d for easing the penetration of the adjacent bone when the plate member 106a is deployed into engagement with the bone. The head 106b also preferably has a tapered configuration, thickening from the tip 106d down towards the legs 106c. Opposing stops 106e are provided at lower faces of the head portion 106b to support the plate member 106a against the body of the bearing member 108 when the plate member 106a is in an undeployed configuration. Similarly, at least one leg 106c is provided with a stop 106f with an abutment surface 106g for interacting with an opposing abutment surface 108b of the securing member receiving portion 108a. Between the opposing legs 106c is a gap 106h for receiving an actuator. An actuator engagement portion in the form of an arcuate interior surface 106i adjacent the gap 106h interacts with the actuator during insertion of the actuator, which causes deployment of the plate member 106a.

The deployable plate members 106a are each received in the securing member receiving portion 108a in restraint portion recesses in the form of generally rectangular openings 108c (FIG. 11) in the bearing member 108. The openings 108c are disposed along the outer lateral side of the upper bearing member 108 and are arranged in a row with the longitudinal aspect of the openings disposed transverse to an anterior-posterior axis 118 of the implant 102. The securing member receiving portion 108a includes a raised ridge 108e that protrudes outwardly beyond an outer bearing surface 108f of the bearing member 108. A cylindrical recess 108g is disposed in the ridge 108e with a longitudinal axis of the recess aligned along the anterior-posterior axis 118 of the bearing member 108 for receiving the actuator in the form of an elongate plunger 112. Plate member gaps 108h in the ridge portion 108e are provided adjacent each opening 108c to provide clearance for the plate members 106a.

Figure 13:
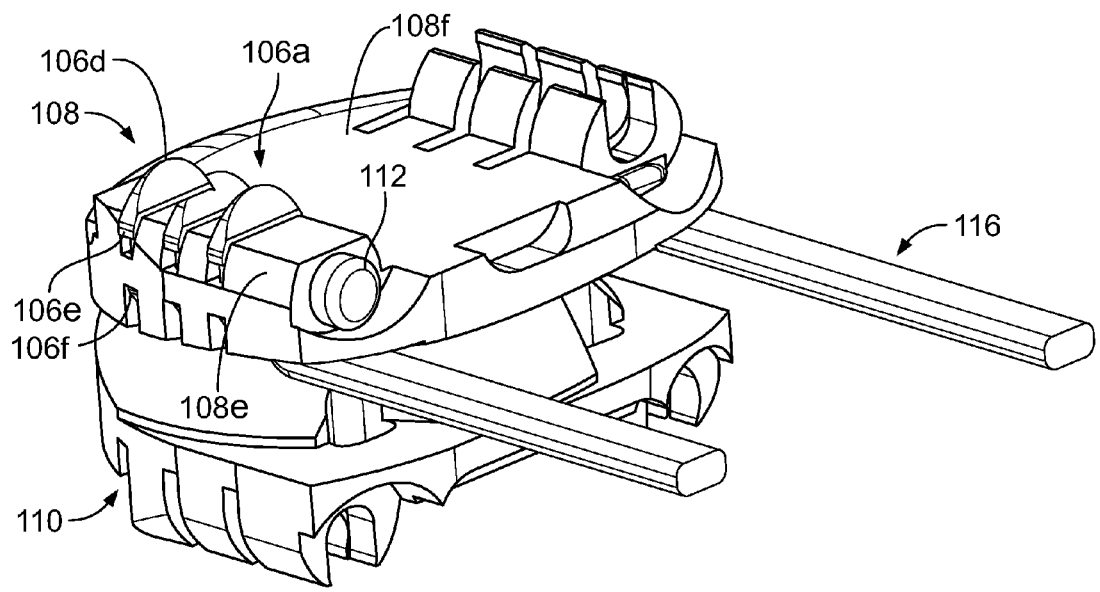
FIG. 13 is an anterolateral perspective view of the intervertebral implant of FIG. 9 showing the deployable securing member in a deployed orientation with the elongate actuating member inserted into the implant body.
Figure 14:
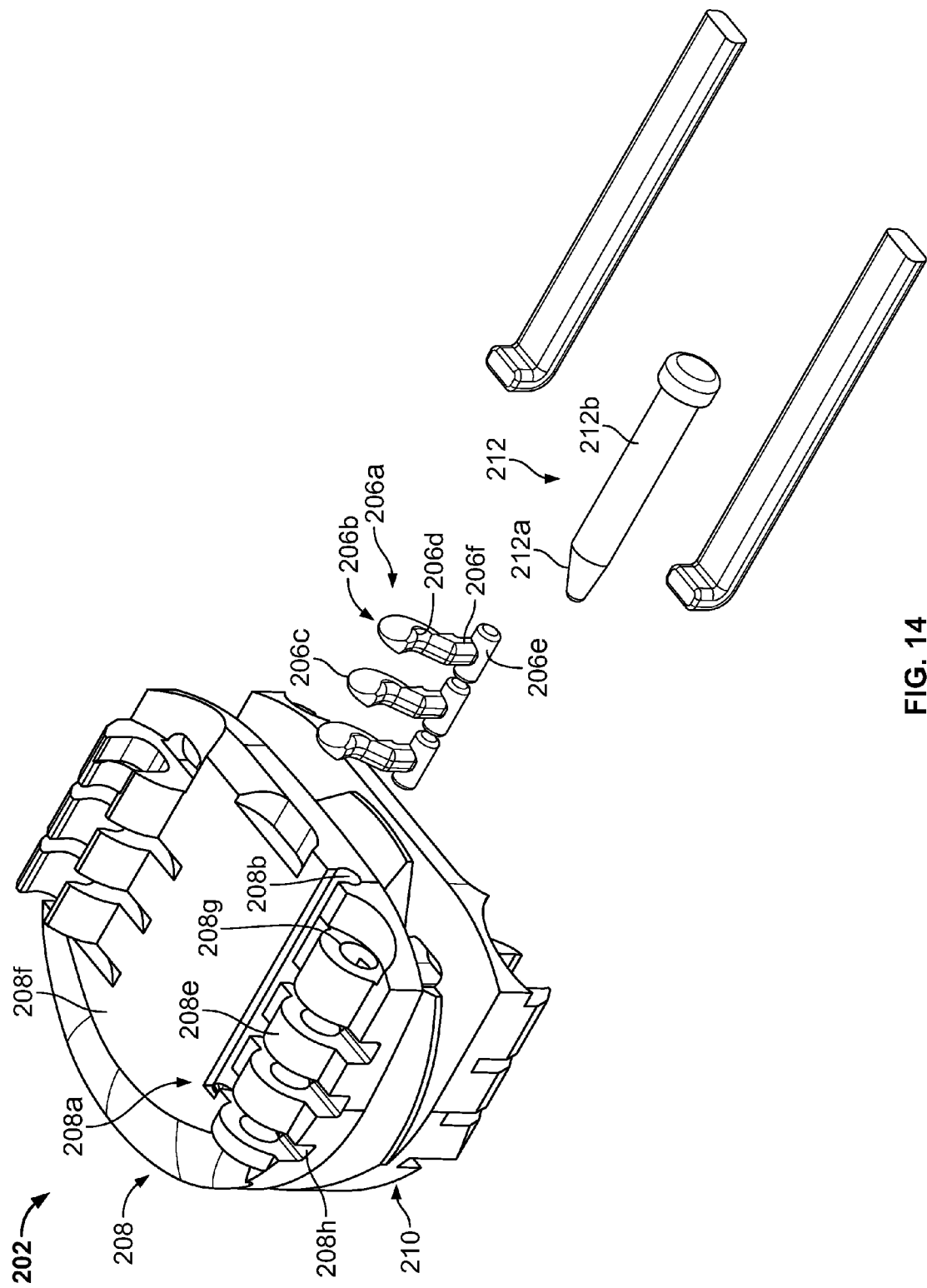
FIG. 14 is an partially exploded anterolateral perspective view of an alternate embodiment of an intervertebral implant with a securing member according to the present invention illustrating a plurality of securing members, an elongate actuating member, and a pair of prongs used for inserting the implant into the intervertebral space.
Figure 15:
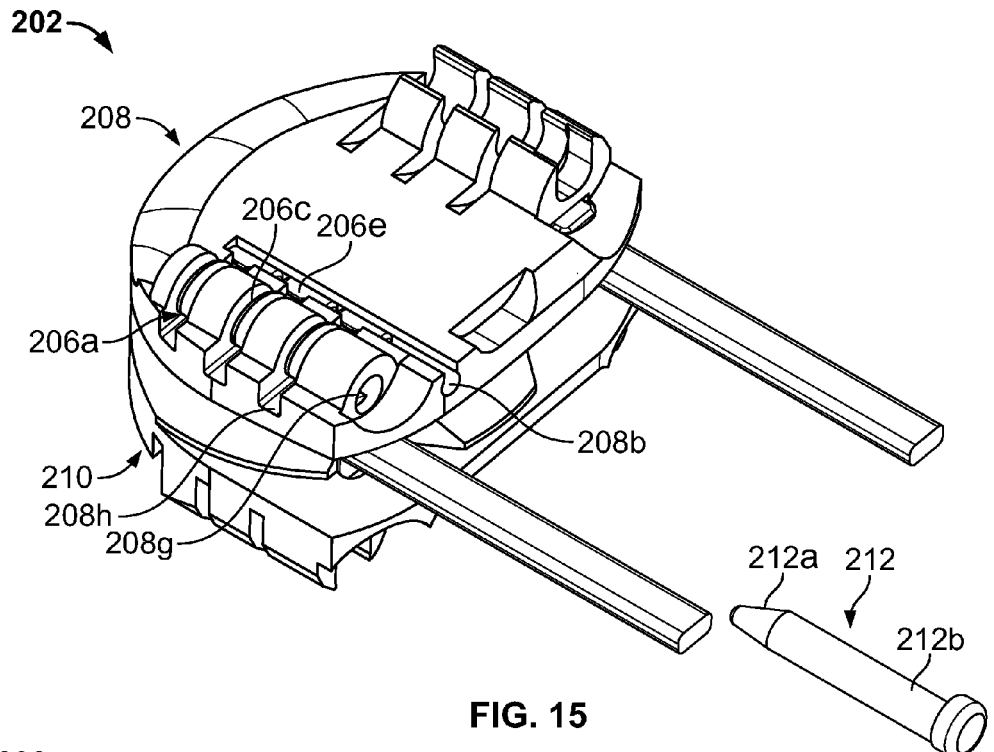
FIG. 15 is an anterolateral perspective view of the implant of FIG. 13 illustrating the plurality of securing members in an undeployed configuration prior to insertion of the actuating member.

In operation, once the vertebrae have been prepared (if at all) to accept the implant 102, the implant 102 is inserted into the intervertebral space using an insertion tool. The deployable securing member 106 is actuated by inserting the elongate plunger 112 into the cylindrical recess 108g of the actuator receiving portion 108d, as shown in FIG. 13. The elongate plunger 112 has a tapered tip 112a to facilitate insertion thereof and gradual deployment of the deployable plate members 106a. During insertion of the elongate plunger 112, the tapered tip 112a biases against the arcuate interior surface 106i, which causes the plate member 106a to be propelled outward towards the adjacent bone. Once the tip 112a progresses past the plate member 106a, the rest of the elongate shaft of the plunger 112 is allowed to pass underneath the interior surface 106i and through gap 106h between the legs 106c. The elongate plunger continues into the next portion of the ridge 108e through cylindrical recess 108g and similarly causes the other plate members 106a to deploy. Once the elongate plunger 112 is fully inserted, the enlarged head portion 112b of the plunger will come into contact with an anterior facing surface 108n of the ridge portion 108e, which keeps the plunger 112 from being inserted too far. Stop 106f keeps the plate members 106a from becoming loose or from being overextended via contact between abutment surface 106g and opposing abutment surface 108b. In the aforementioned configuration, the plate members are deployed straight up or linearly into the vertebrae, without any rotational displacement of the plate members 106a. This embodiment is advantageous because the restraining portions do not pull the implant 102 further into the intervertebral space, which can bring the implant out of the desired position, or cause trauma to the surrounding tissue and blood vessels. The plate members 106a are allowed to be retracted by removing the plunger from the receiving portion 108a.

The lateral orientation (i.e., transverse to the anterior-posterior axis) of the plate members 106a is advantageous for providing superior resistance to migration in the anterior or posterior direction of the implant. However, the plate members 106a may be oriented in other configurations.

The following description of the general features of a preferred embodiment of an intervertebral implant according to the present invention is described with respect to the embodiment in FIGS. 9-13. However, the general features described below may be implemented in any of the embodiments described herein.

It is preferred that the footprint of the artificial disc devices herein be similar to the footprint of the endplate although generally smaller to fit within the intervertebral space. The outer bearing surfaces 108f are preferably contoured to match the contour of the endplates. For example, if the surgeon prepares the endplates to be flat, it is preferred that the outer bearing surfaces 108f, 110a are also flat. Likewise, if the endplates are prepared to be concave, it is preferred that the outer bearing surfaces 108f, 110a are similarly convex. It should be noted that endplates that are concave will generally retain the artificial disc device better since the device becomes cupped between the vertebrae.

Figure 9:
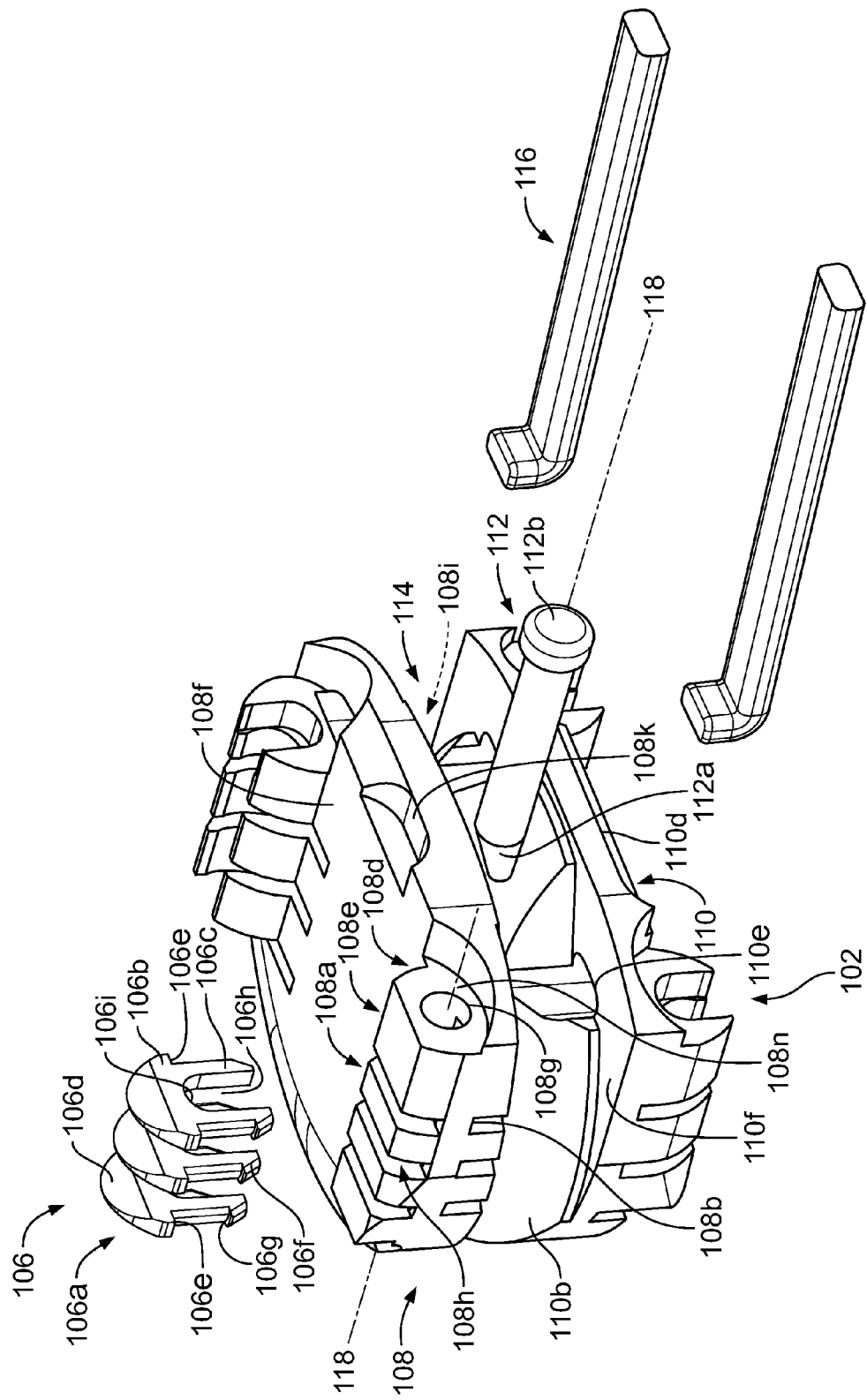
FIG. 9 is a partially exploded anterolateral perspective view of an alternate embodiment of an intervertebral implant according to the present invention illustrating a plurality of securing members of the securing member, an elongate actuating member, and a pair of prongs used for inserting the implant into the intervertebral space.

FIG. 9 shows an artificial disc implant 102 with upper and lower bearing members 108, 110 having a bearing interface 114 therebetween that allows the members 108, 110 to shift or articulate relative to each other when implanted and secured in an intervertebral space. The bearing interface 114 includes concave recess 108i (FIG. 10) formed in the inner or lower surface 108p of the upper bearing member 108 and a substantially convex portion 110b that projects up from inner or upper surface 110f of the lower bearing member 110. Although not preferred, the concave and convex portions 108i, 110b may be switched such that the upper bearing member 108 may alternatively comprise the convex portion 110b. The securing members according to the present invention may be utilized with unitary implants, such as spinal cages and spacers, as well as multi-piece implants, such as the motion-preserving intervertebral implants disclosed in the drawings.

The convex portion 110b comprises a convex articulation surface 110c, and the concave portion 108i comprises a concave articulation surface 108j. It is preferred that the articulation surfaces 110c and 108j have substantially matching geometries or radii of curvature although some mismatch of curvature may be desired to provide a combination of rolling and sliding motion to occur between the articulation surfaces 110c and 108j. U.S. Provisional Application 61/050,612 filed May 5, 2008 discloses a "ball-in-bowl" configuration for the articulation surfaces, and is hereby incorporated by reference in its entirety. In particular, the concave articulation surface 108j may have two different radii of curvature, such that one portion of the concave articulation surface 108j has a first radius of curvature, and a second portion of the concave articulation surface 108j has a second, larger radius of curvature. The first radius of curvature is preferably the same as the radius of curvature of the convex articulation surface 110c, such that rotational sliding may occur between the articulation surfaces 108j, 110c. When the joint is extended, the concave articulation surface 108j is allowed to translate slightly due to the mismatch in curvature between the first radius of curvature of the convex articulation surface 110c and the second, larger radius of curvature of the concave articulation surface 108j. This configuration allows for a greater range of motion and a more natural movement of the joint.

Figure 10:
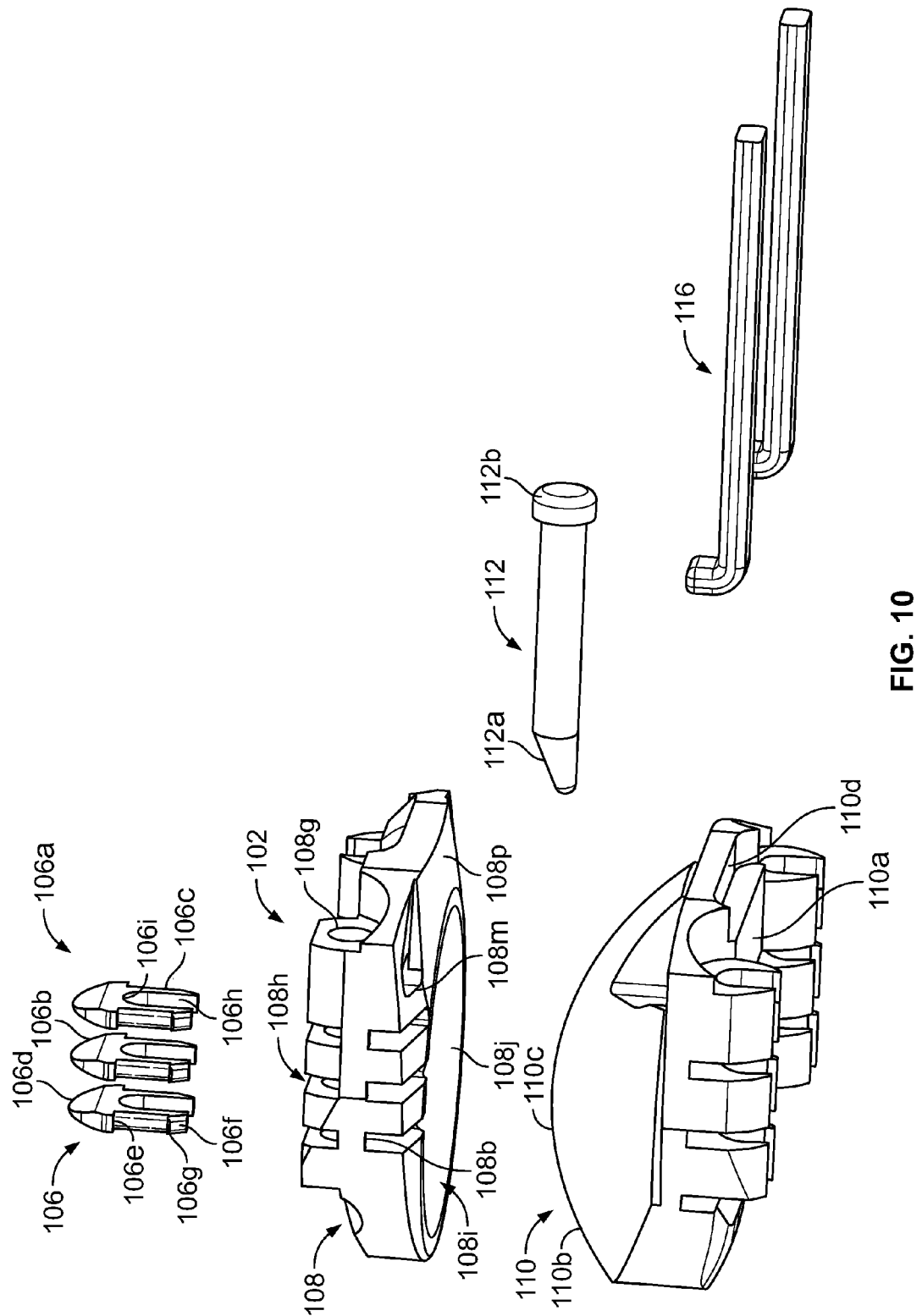
FIG. 10 is an exploded anterolateral perspective view of the invetervertebral implant of FIG. 9.
Figure 11:
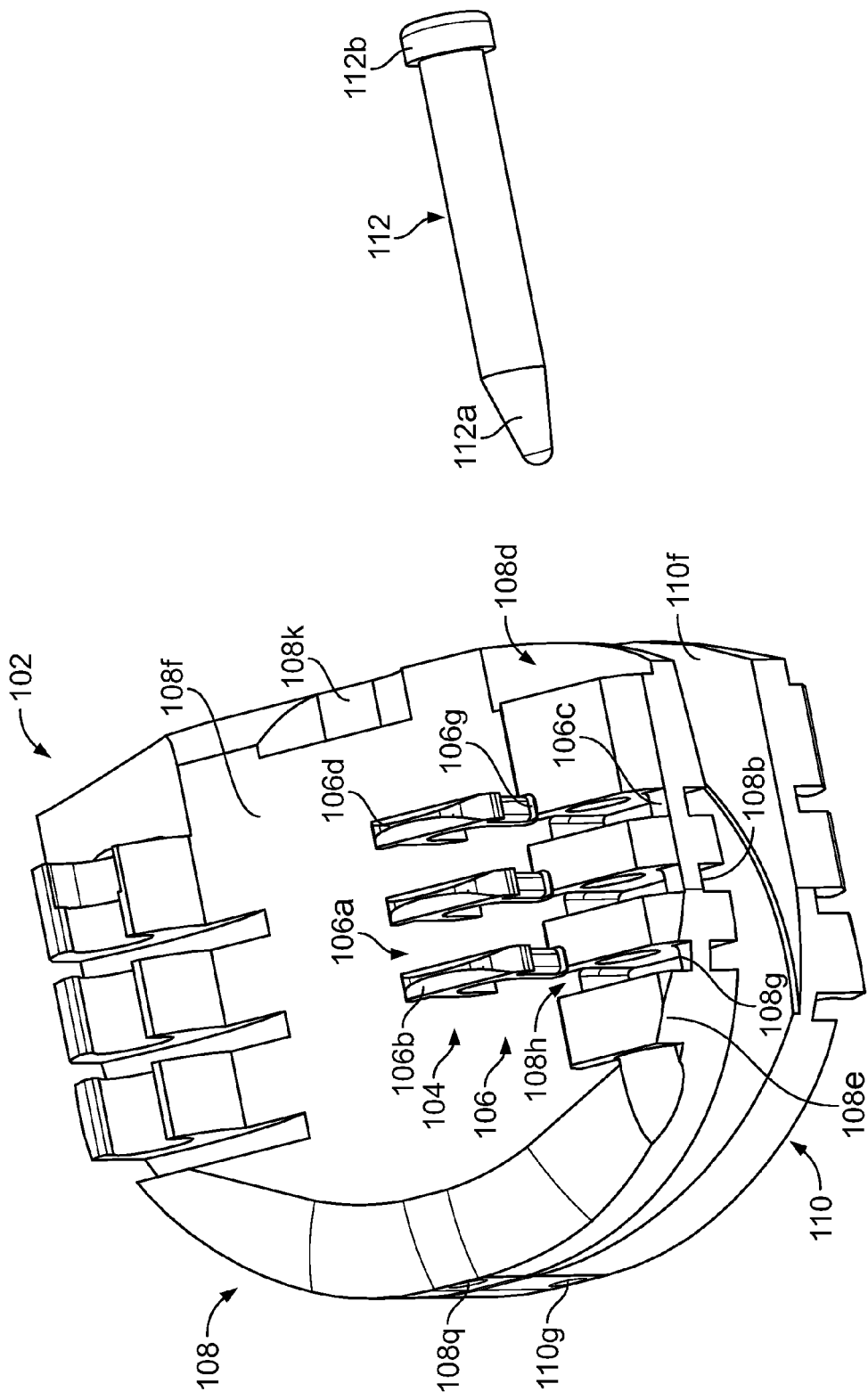
FIG. 11 is an exploded posterolateral perspective view of the intervertebral implant of FIG. 9.
Figure 12:
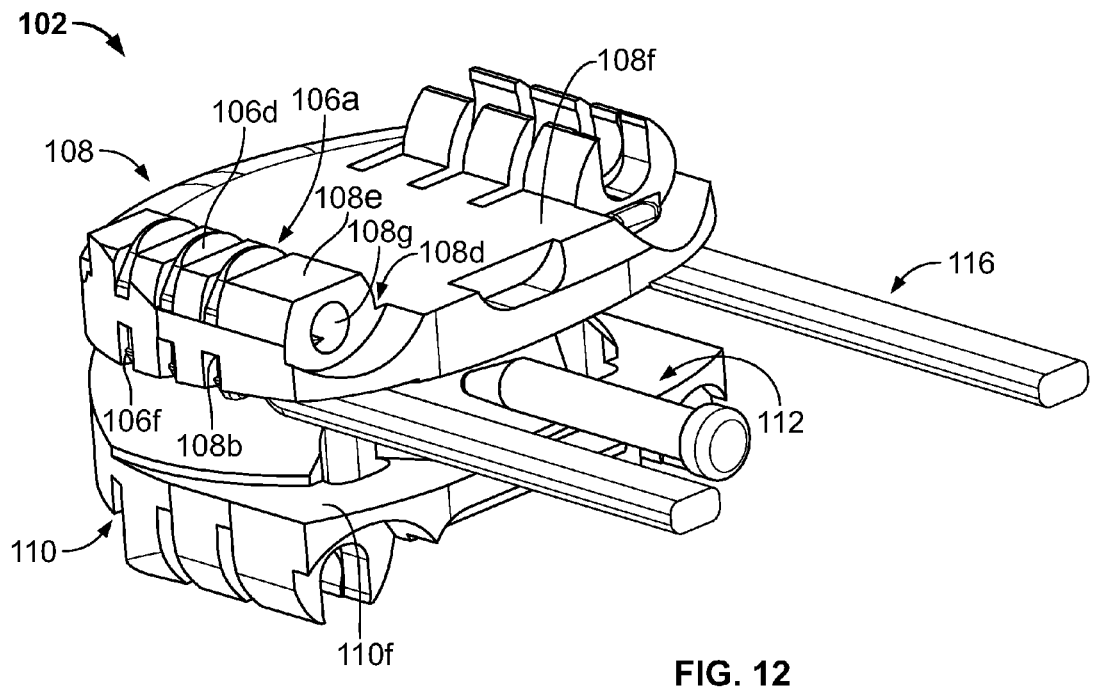
FIG. 12 is an anterolateral perspective view of the intervertebral implant of FIG. 9 illustrating the prongs secured to the upper bearing member for manipulation of the implant and the elongate actuating member positioned remotely from the deployable securing member prior to insertion thereof.

As discussed above, the geometries may be complex in nature but preferably are ball and socket style. The convex portion 110b and concave portion 108i may extend substantially to the outer perimeter of the bearing member 108, 110 as illustrated in FIGS. 9 and 10, or may be formed, typically with a smaller radius of curvature inward a predetermined distance from the outer perimeter of the bearing member 108, 110. Each bearing member 108, 110 is preferably manufactured from PEEK (polyetheretherketone) or fiber reinforced PEEK or other biocompatible polymer combination or radiolucent material demonstrating very low surface wear in high repetition wear testing.

The disc implant 102 according to the present embodiment has docking features for attaching the implant 102 to an insertion tool. The lower bearing member 110 has a shelf-like platform 110d along its anterior face for providing a contact surface for the implant insertion tool. Similarly, the upper bearing member 108 has a shelf 108k on its anterior face for providing a contact surface for the insertion tool. The internal facing surfaces 108p, 110f of both bearing members 108, 110 each have a pair of generally rectangular recesses 108m, 110e disposed thereon to accept gripping members of the insertion tool. Two of the gripping members, prongs 116, are shown with the implant 102 for reference. The prongs 116 engage the upper bearing member 108 within recesses 108m during insertion of the implant 102. Preferably, two additional prongs are provided with the insertion tool for engaging with recesses 110e to work in tandem with prongs 116. These docking features are advantageous because the insertion tool manipulates the implant 102 substantially within the overall footprint of the implant 102. This prevents trauma to the surrounding tissue and bone during insertion of the implant 102 and removal of the inserter after the implant 102 is inserted.

Once the implant 102 is secured to the inserter, the disc implant 102 is then inserted into the intervertebral space. The position of the implant 102 may be determined using fluoroscopy to view the orientation of the implant 102. Tantalum markers 108q, 110g (FIG. 11) disposed in the posterior face of both the upper and lower bearing members 108, 110 allow the surgeon to identify and position the posterior end of the implant 102. In addition, the securing member(s) 106, which are also radiopaque when made out of titanium or stainless steel, may be used to determine the orientation of the implant 102.

In another form in accordance with the present invention illustrated in FIGS. 14-17, an intervertebral implant 202 with a deployable securing member is disclosed. The implant body is similar to that of the embodiment shown in FIGS. 9-13. However, the securing member is comprised of deployable arms 206a which may be rotated about a pivot into engagement with the bone. The arms 206a are deployed via an elongate plunger 212 similar to that of the embodiment disclosed in FIGS. 14-17. The deployable arms are preferably rotatable about an anterior-posterior axis such that the deployable arms 206a are disposed transversely to the anterior-posterior axis and translation thereof into a deployed position does not cause shifting of the implant 202.

The securing member is provided with three deployable arms 206a having bone engaging head portions 206b. The head portion 206b preferably has a sharpened outer edge 206c for easing penetration of the head portion 206b into the bone. The head portions 206b have a generally arcuate profile, with a convex outer edge 206c and a concave inner surface 206d for engaging with the arcuate outer surface of the elongate plunger 212. Each head portion 206b is connected to a transverse shaft 206e via a neck portion 206f. The transverse shaft 206e is cylindrically shaped for being pivotally captured within similarly-shaped channel 208b. The transverse shaft 206e is held within the channel 208b with a friction fit so that no additional fasteners or pieces are required to connect the restraining portions to the implant 202. This construction simplifies manufacture and assembly, and increases the robustness of the implant. Because intervertebral implants in particular may be very small in many applications, it is desirable for such implants to have few components. For example, a cervical disc implant may only be 5 mm high. Thus, these kinds of implants must have components that are sturdy and robust enough to be functional on a very small scale.

The securing member receiving portion 208a has a similar configuration to that of the embodiment described in FIGS. 9-13. A cylindrical ridge portion 208e protrudes outwards from the outer bearing surface 208f and contains a cylindrical recess 208g for receiving the elongate plunger 212. Lateral channels 208h disposed in the bearing member and the cylindrical ridge portion 208e extend transversely to the cylindrical recess 208g for receiving the deployable arms 206a. The lateral channels 208h are in communication with channel 208b. When the deployable arms 206a are configured within the lateral channels 208h in an undeployed orientation, the arms 206a remain within the profile of the bearing member and the ridge 208e for ease of insertion of the implant into the intervertebral space.

Figure 16:
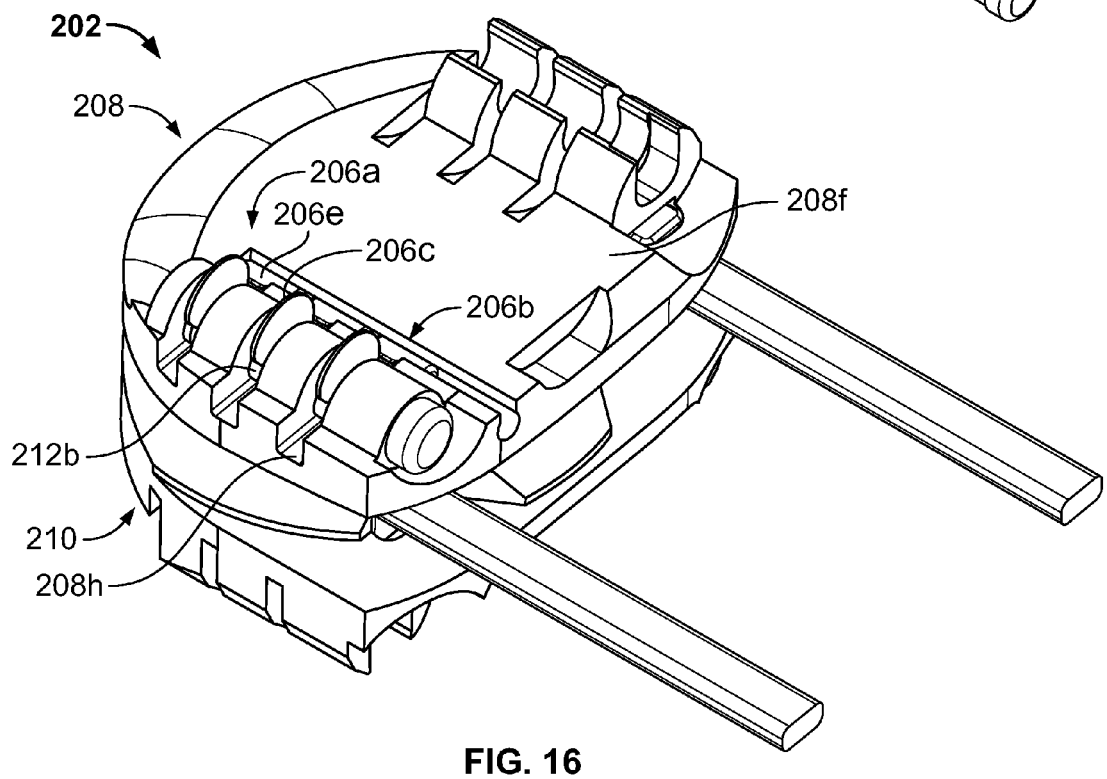
FIG. 16 is an anterolateral perspective view of the intervertebral implant of FIG. 14 showing the deployable securing member in a deployed configuration with the elongate actuating member inserted into the implant body.
Figure 17:
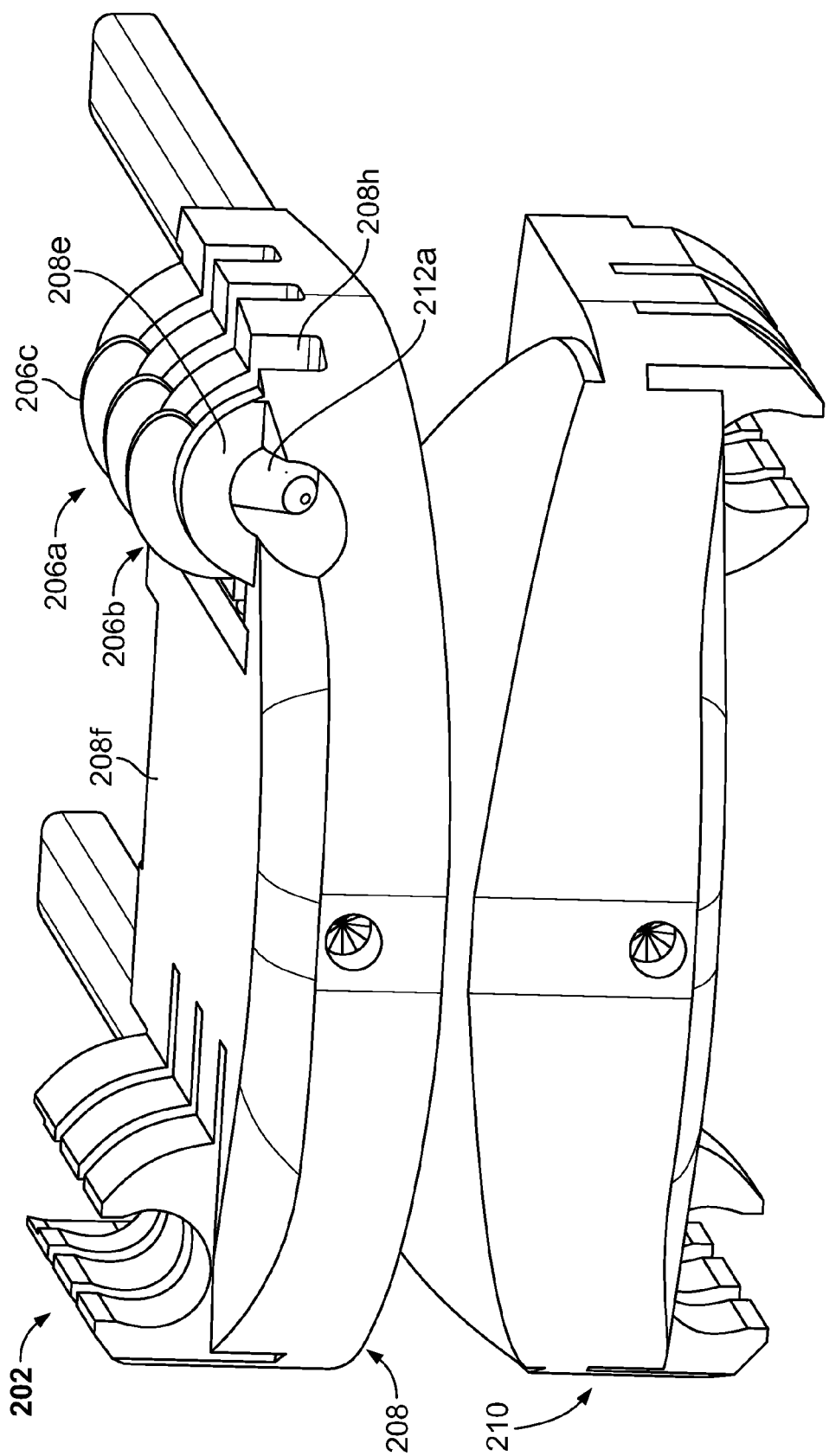
FIG. 17 is a posterolateral perspective view of the implant of FIG. 14.
Figure 18:
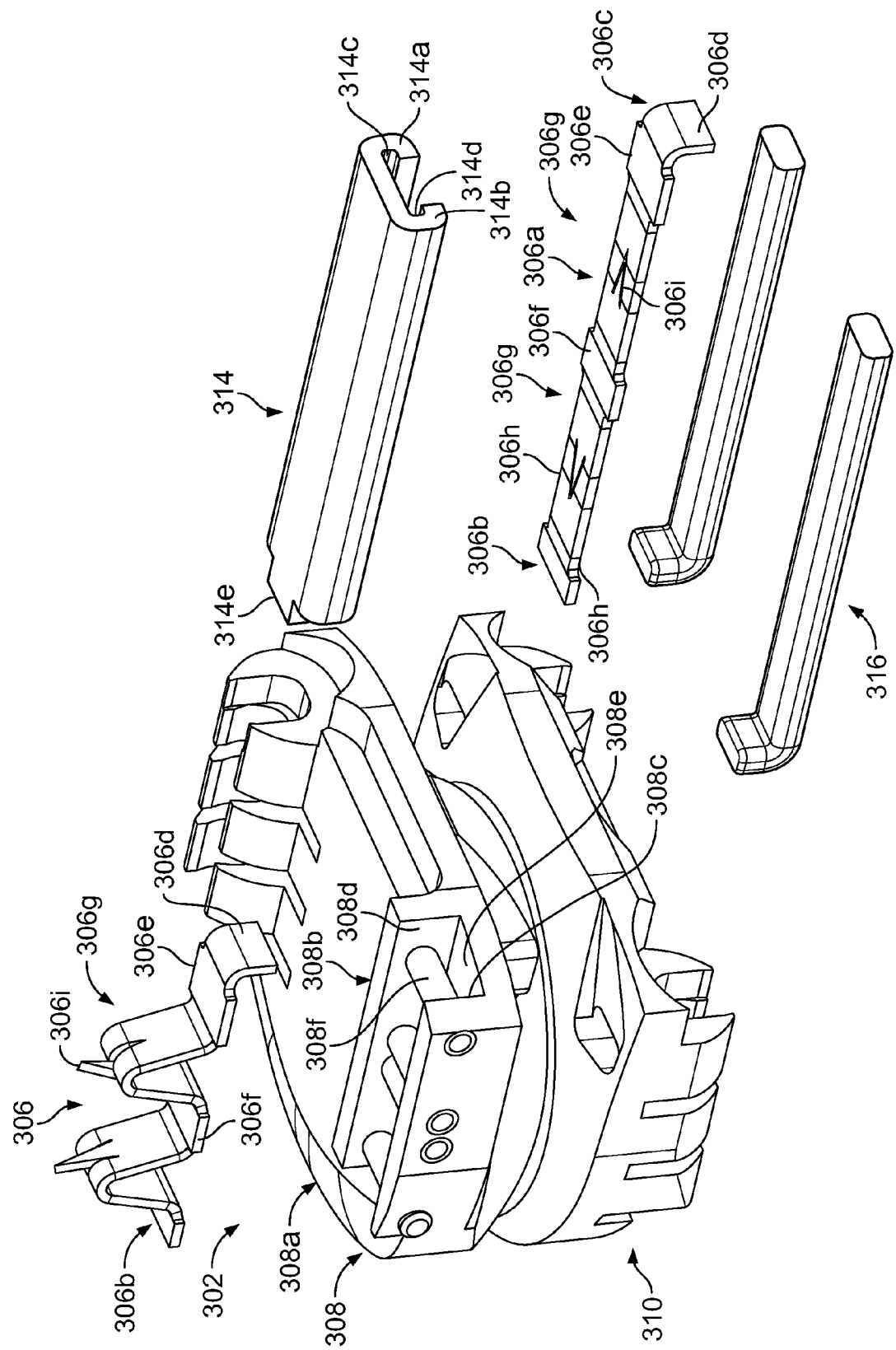
FIG. 18 is a partially exploded anterolateral perspective view of an alternate embodiment of an intervertebral implant with a securing member according to the present invention illustrating the securing member in a deployed and an undeployed configuration, a securing member inserter, and a pair of prongs used for inserting the implant into the intervertebral space.

To actuate and deploy the deployable arms 206a, the plunger 212 is inserted into the cylindrical recess 208g. The tapered tip 212a interacts with the concave inner surface 206d of the deployable arm 206a, gradually biasing the arm 206a upward, causing the arm 206a to rotate about the transverse shaft portion 206e. The deployable arm 206a is deployed fully to its maximum height once the plunger tip extends beyond the concave inner surface 206d, such that the deployable arm 206a rests on top of and is supported by the shaft 212b of the plunger 212. As shown in FIGS. 16 and 17, the deployable arms protrude substantially above the ridge 208e such that they are operable to engage with the adjacent bone for fixing the implant to the vertebra.

In another form in accordance with the present invention, an intervertebral implant 302 having a deployable securing member 306 for affixing the implant to the adjacent vertebra is disclosed in FIGS. 18-21. In the present form, the securing member 306a takes the form of a deformable or bendable elongate member 306a that may be inserted into the securing member receiving portion 308a and bent into a form causing bone engaging projections to engage with the adjacent vertebra.

The bendable elongate member 306a is preferably a flat elongate member having a longitudinal length between its ends and a width. The elongate member 306a has a leading end 306b with an enlarged width that is inserted first into the receiving portion 308a. A trailing end 306c is provided with a transverse tab portion 306d transverse to the longitudinal length thereof for manipulating the elongate member 306a and providing a stop to keep the elongate member 306a from being inserted too far into the intervertebral space. The trailing end 306c is also provided with a guide portion 306e having an enlarged width for guiding the elongate member 306a within the insertion instrument 314 and the securing member receiving portion 308a. In addition, a central guide portion 306f is positioned between the two ends for guiding the elongate member 306a. In between either end 306b, 306c and the central guide portion 306f is a bending zone 306g which is configured for being bent during insertion of the elongate member 306a and protruding upwardly or outwardly into engagement with the adjacent bone. The bending zone 306g preferably includes perforations or weakened portions 306h to promote bending at a predetermined location on the elongate member 306a. In a preferred embodiment, the bending zones 306g include a preformed protrusion or spike 306i which lies within the elongate member prior to bending thereof. When the elongate member 306a is bent, the bending zones are forced into an inverse V shape, causing the spike 306i to be deployed upwards into the adjacent bone. Although the elongate member 306a is shown with two bending zones 306g and spikes 306i, the elongate member 306a may be provided with different numbers of bending zones and spikes. Although the bendable elongate member has portions bent into a V shape, other shapes and configurations are contemplated.

Figure 21:
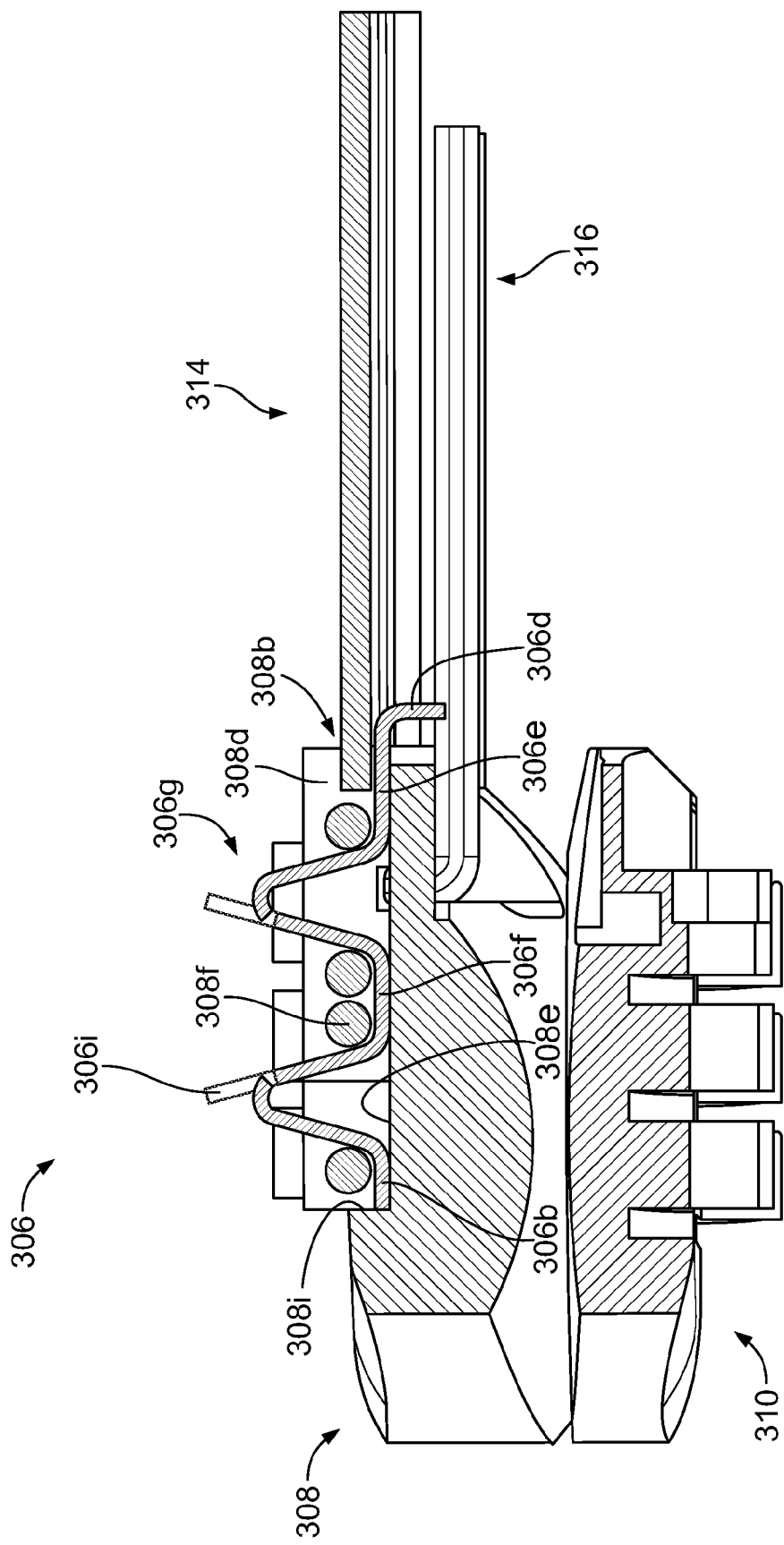
FIG. 21 is a lateral cross-section along an anterior-posterior axis of the implant of FIG. 18 illustrating the securing member in a deployed configuration.
Figure 22:
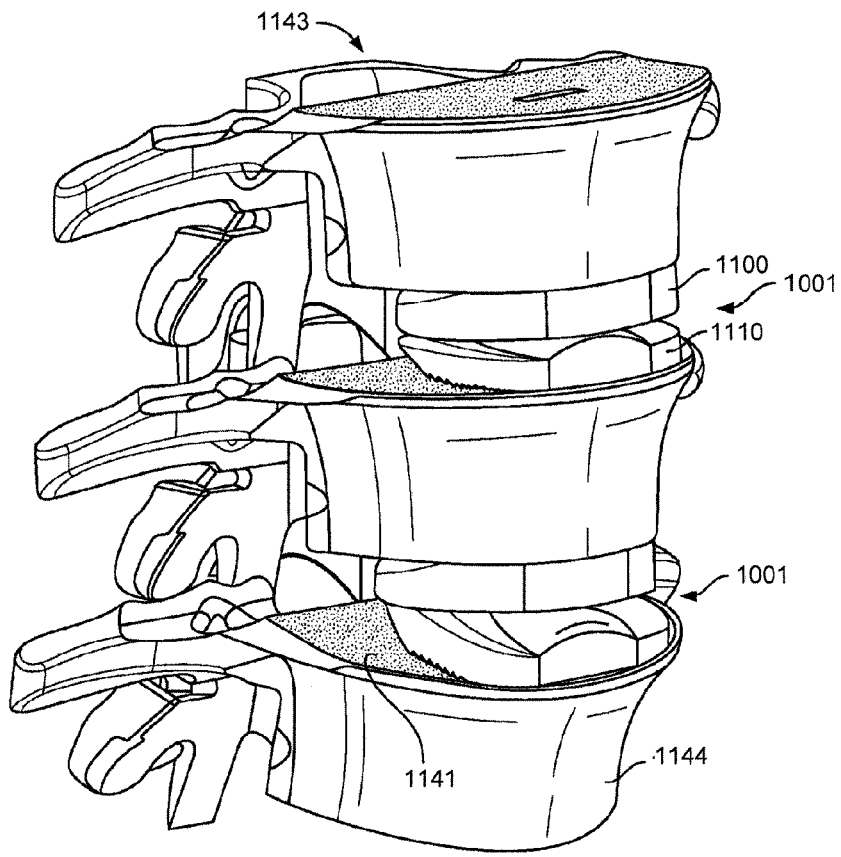
FIG. 22 is a perspective view of an anterior portion of the spine with two implants according to the present invention disposed within the intervertebral spaces.
Figure 23:
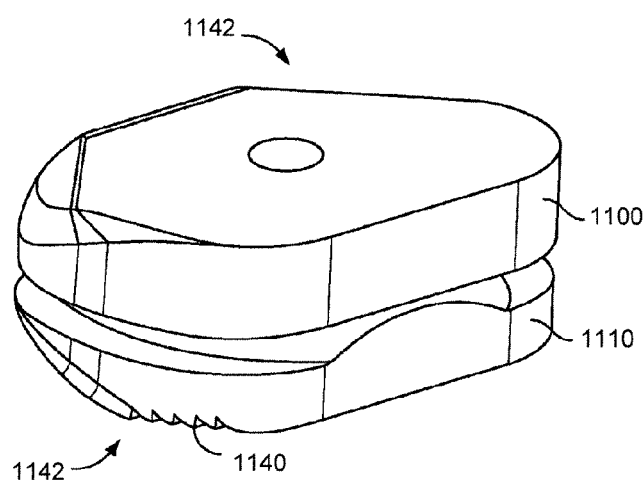
FIG. 23 is an anterolateral perspective view of an implant according to the present invention.

The securing member receiving portion 308a takes the form of a generally U-shaped channel 308b disposed along a lateral edge on the upper bearing member 308. The channel 308b has opposing side walls 308c, 308d and a bottom surface 308e extending between the two side walls 308c, 308d. Extending between the side walls 308c, 308d are restraining members in the form of pins 308f. The pins 308f are operable to restrain the elongate bending member 306a from bending at predetermined locations. Pins 308f are preferably cylindrical or have radiused edges to prevent stress concentrations on the bending member 306a and to reduce friction thereon during bending. Thus, the pins are located in positions corresponding to positions on the elongate bending member 306a that are to remain unbent. The weakened portions 306h on the elongate member 306a are preferably aligned with the pins 308f, such that when the bending member is inserted into the receiving portion 308a, the bending member will bend in the open areas between the pins 308f. As shown in FIG. 21, the pins 308f are positioned above the bottom surface 308e such that the elongate member 306a is held relatively snug therebetween. The channel 308b has an end wall 308j operable to provide a stop for the bending member 306a, as well as a surface to compress the bending member 306a against to cause bending of the bending zones 306g and deployment of spikes 306i.

The insertion instrument 314 comprises a generally C-shaped housing with opposing arms 314a, 314b to provide opposing grooves 314c, 314d in which the bending member may be inserted for guiding the bending member into the securing member receiving portion. The widened ends 306b, 306c and central portion 306f fit within the grooves 314c, 314d. The transverse tab portion 306d is sized and configured to fit between the opposing arms 314a, 314b such that it may pass therebetween. This way, the bending member 306a may be pushed into the receiving portion via the transverse tab portion 306d. The insertion instrument 314 is also provided with an extended lip 314e on the insertion end for providing the bending member 306a with additional support to prevent bending of the member 306a as it leaves the insertion instrument 314 and prior to reaching the first pin 308f at the entrance of the channel 308b at the anterior side of the implant 302.

Figure 19:
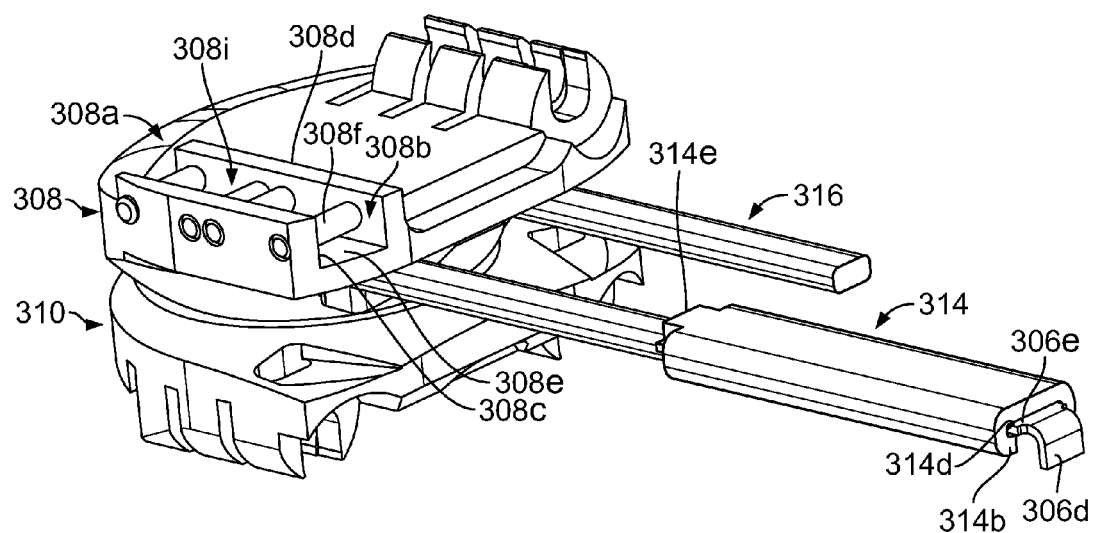
FIG. 19 is an anterolateral perspective view of the intervertebral implant of FIG. 18 illustrating the securing member disposed within the securing member inserter.
Figure 20:
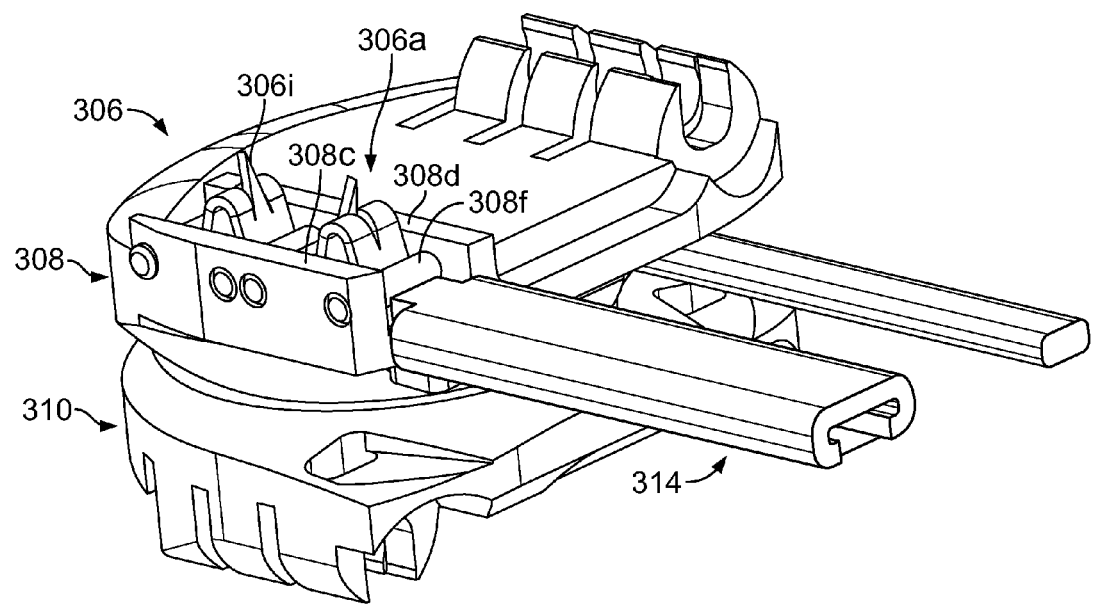
FIG. 20 is an anterolateral perspective view of the implant of FIG. 18 illustrating the securing member in a deployed configuration.

In operation, the implant 302 is first inserted into the prepared intervertebral space via an implant insertion instrument, which includes prongs 316 which grasp the implant 302 in opposing recesses on the inner facing surface of the upper bearing member 308, as shown in FIG. 21. Next, the bending member 306a is slid into the grooves 314c, 314d of the insertion instrument as shown in FIG. 19. Then, the insertion instrument 314 is positioned adjacent the receiving portion 308a such that the elongate member 306a is aligned with the channel 308b. The bending member 306a is then pushed into the channel 308b between the pins 308f and the bottom surface of the channel 308e via the transverse tab portion 306d. Once the insertion end 306b of the bending member 306a reaches the abutment surface 308j, further insertion of the bending member 306a will cause compression and the bending member 306a will begin to bend or deform. This deformation begins at the weakened portions 306h and causes the bending zones 306g to deform upwards into engagement with the adjacent bone. As the bending zone 306g begins to bend at its peak, the barb or spike 306i will be deployed upwards into the bone. Once the bending member 306a has been fully inserted into the receiving portion, the insertion instrument 314 may be removed from the implant site. Further details of the preparation of the vertebrae, insertion procedure and insertion tool may be found in U.S. patent application Ser. No. 11/856,667, which is incorporated by reference herein.

The securing member receiving portion 308a for the elongate bending member 306a is shown in FIGS. 18-21 in one location on the implant; however, it is contemplated that the upper and lower members 308, 310 may include securing members 306 in more than one location. Further, all of the securing members shown and described herein may be implemented together with different types of securing members, such as those shown and described above or other securing members and restraining members known in the art. However, in a preferred form, an implant according to the present invention comprises two securing members of similar configurations on each bearing member.

Figure 24:
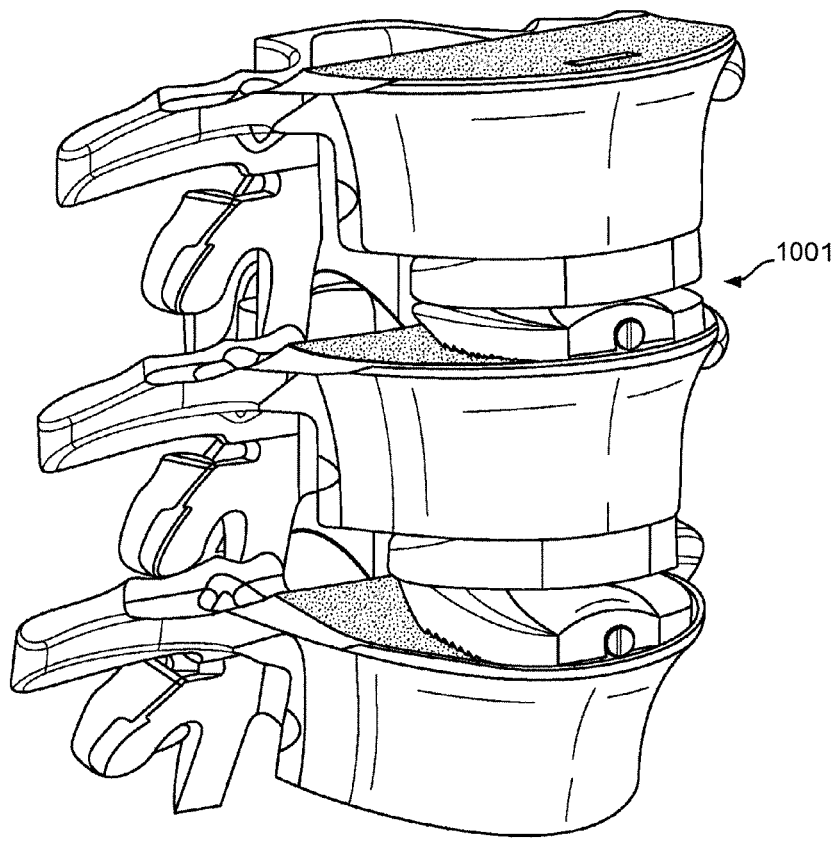
FIG. 24 is an anterolateral perspective view of an implant with a securing mechanism according to the present invention implanted within the intervertebral space.
Figure 25:
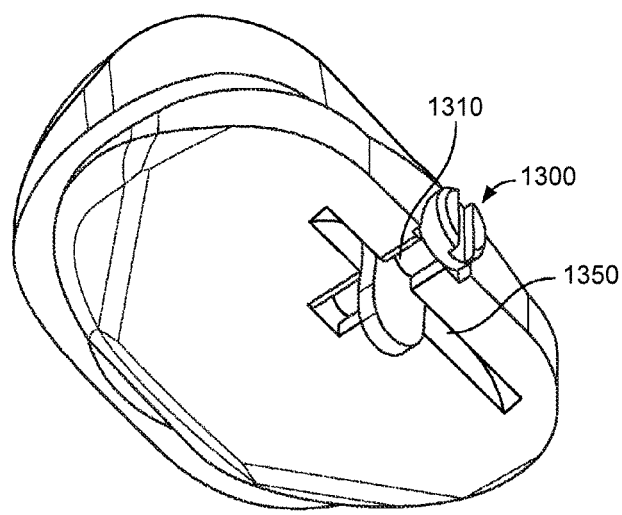
FIG. 25 is a perspective view of a bearing surface of an implant component with a securing mechanism according to the present invention.
Figure 26:
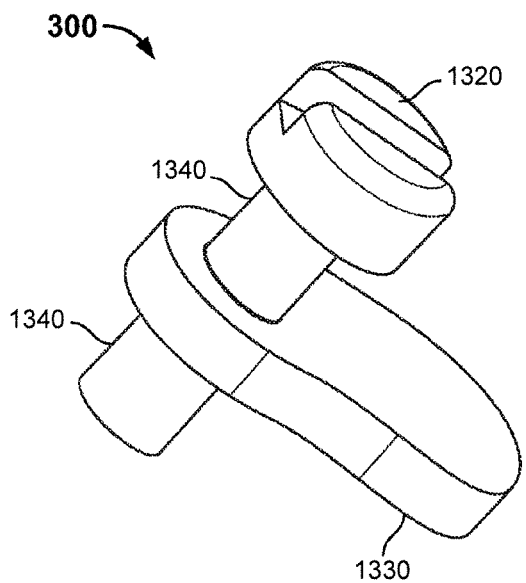
FIG. 26 is a perspective view of a securing component in the form of a deployable paddle or cam according to the present invention.
Figure 27:
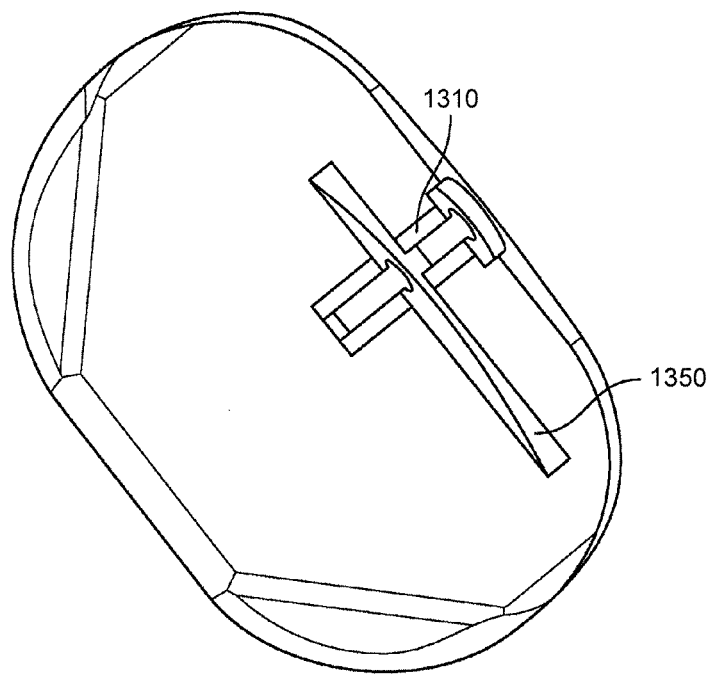
FIG. 27 is a perspective view of a bearing surface of an implant component with a deployable securing mechanism according to the present invention.
Figure 28:
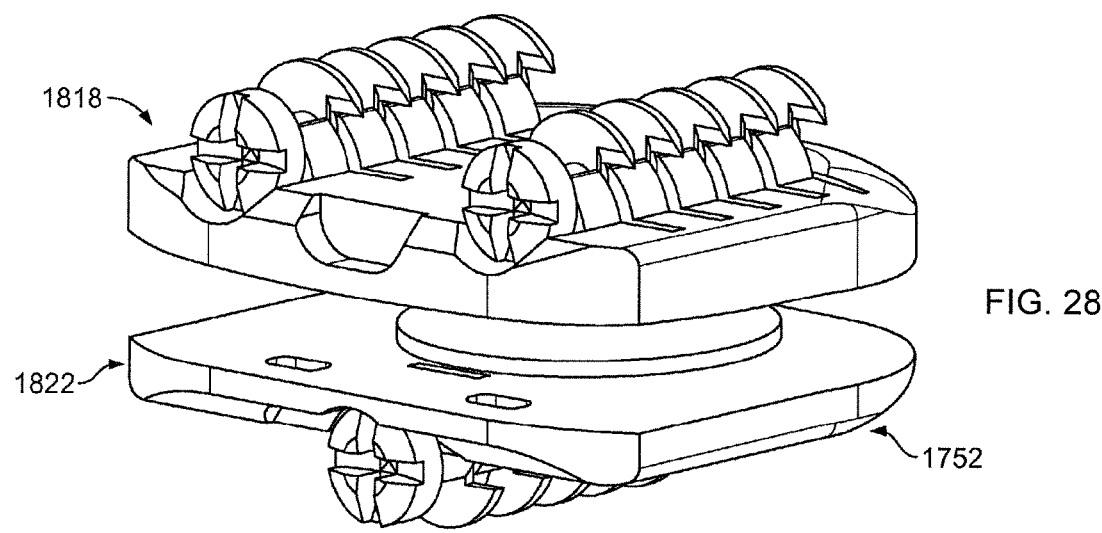
FIG. 28 is an anterolateral perspective view of an artificial disc implant according to the present invention with the securing mechanisms fully deployed.

In an alternative embodiment, the artificial disc device 1001 shown in FIG. 24 comprises a restraint portion 1220 in the form of a deployable paddle 1300. The paddle 1300 is housed within one of the shell members 1100, 1110 as illustrated in FIG. 25. The paddle 1300 may be manufactured from an array of biocompatible materials including but not limited to polymers such as PEEK or metals such as titanium or stainless steel alloys although radiolucent materials are preferred. In a preferred orientation, the paddle 1300 is secured within the body of a shell 1100, 1110 by a paddle restraint 1310 in this case in the form of a snap joint. The paddle comprises a restraint arm 1330 that may be deployed into the endplate 1141 of the vertebrae 1143 upon rotation of the drive head 1320 with the proper instrument. The restraint arm 1330 may include a sharpened edge if so desired. The neck portion 1340 of the paddle 1300 is held by the paddle restraint 1310 and is preferably configured with a profile suitable for rotation. The restraint arm 1330 may include apertures or slots to encourage bone growth through the restraint arm 1330.

The endplate facing surface 1142 comprises a restraint recess 1350 to accommodate the paddle 1300 and the restraint arm 1330 during implant insertion. Once the disc device 1001 is inserted, the restraint arm 1330 may be deployed into the endplate to secure the device 1001 in the desired location between the vertebrae. Several of the disclosed embodiments may require the surgeon to prepare the vertebral body 1144 to accept restraint portions that are intended to become integrated into the bone. In most cases, this preparation involves removing bone and creating restraint access typically in the form of a recess, channel, slot or profile similar to the restraint feature. Obviously, the size of the restraint portion will affect the size of the restraint access. Therefore it is beneficial that restraint portions that interfere with the bone are suitably sized to prevent an oversized restraint access that compromises the vertebrae 1143 and risks vertebrae 1143 fracture. It is preferable that both the restraint access and restraint portion have radiused edges to reduce stress concentrations in the vertebral body.

Figure 29:
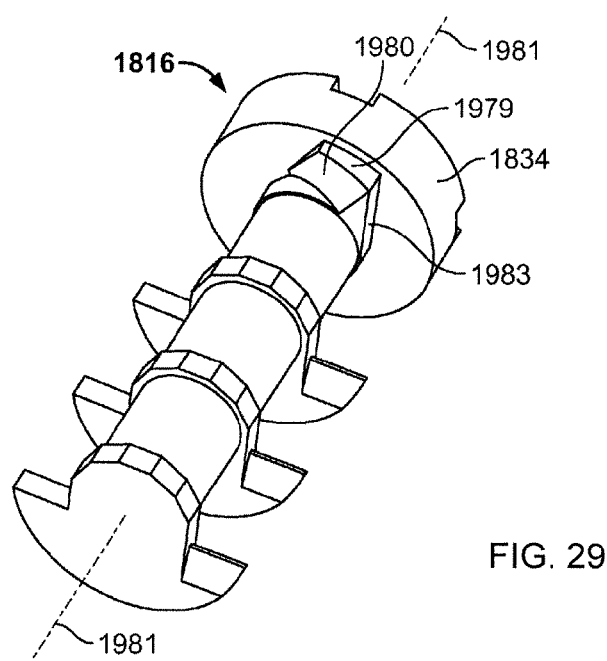
FIG. 29 is a posterolateral perspective view of a cam shaft securing mechanism according to the present invention illustrating a camming surface.
Figure 30:
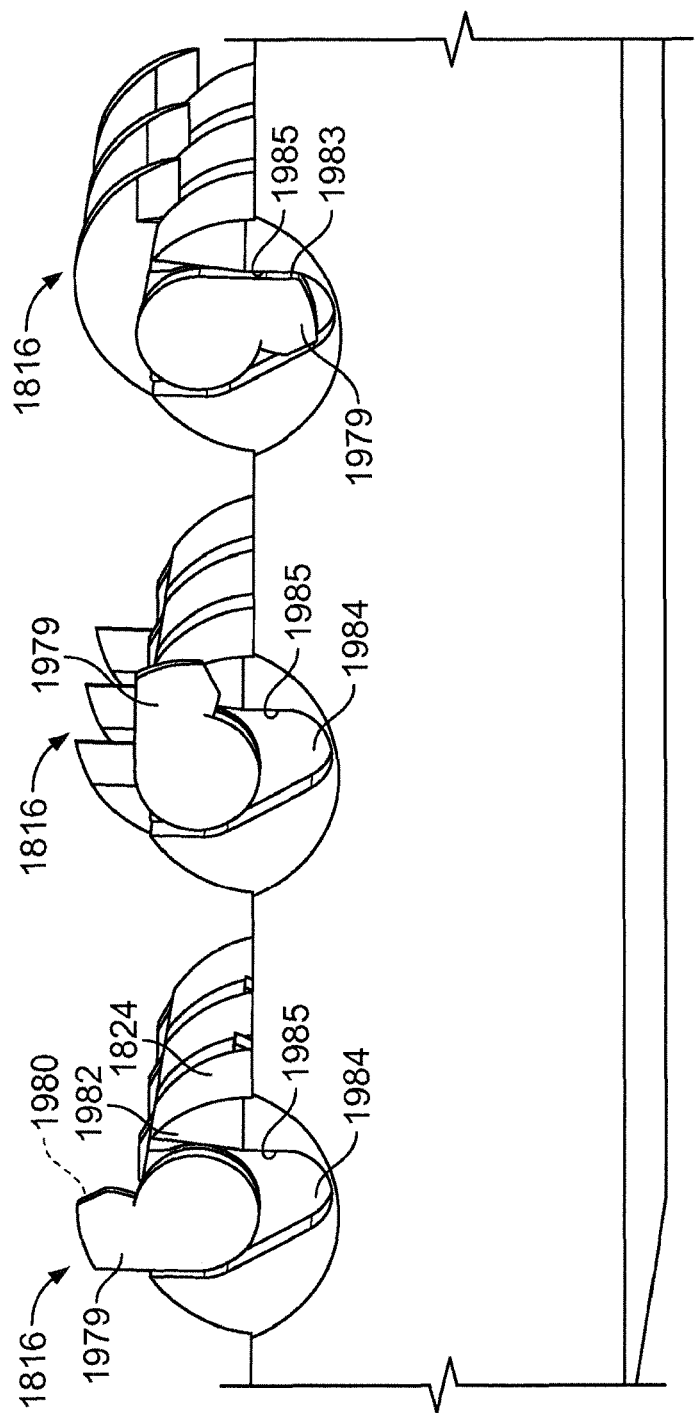
FIG. 30 is an anterolateral perspective view of the cam shaft of FIG. 29 with the head hidden disposed in a test block mimicking a securing mechanism for an implant for illustration of the operation of the cam shaft. The cam shaft is shown in an undeployed position, a partially deployed position, and fully deployed, from left to right.
Figure 31:
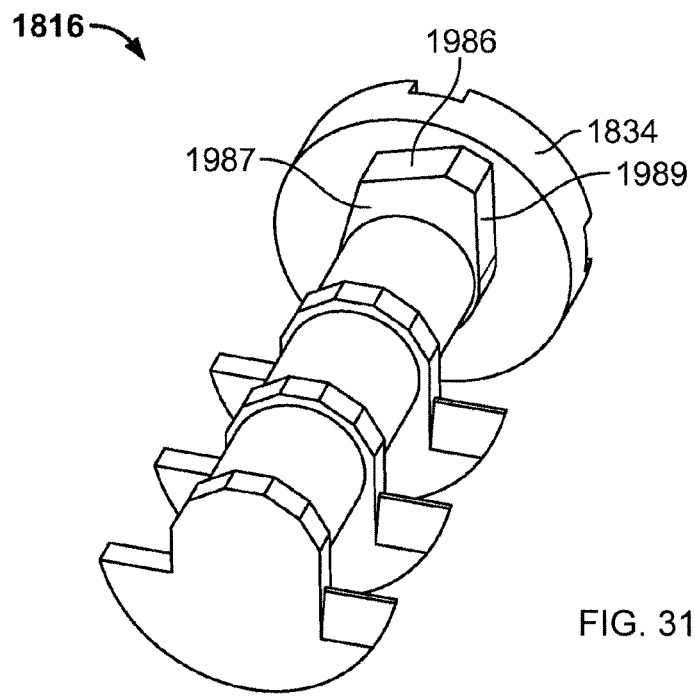
FIG. 31 is a posterolateral perspective view of a cam shaft securing mechanism according to the present invention illustrating a flat camming surface.

The securing mechanism may take many forms. In one embodiment according to FIG. 29, the securing mechanism takes the form of a cam shaft 1816. The cam shaft 1816 has a radially extending cam projection 1979 including a tactile feedback creating surface in the form of a wedge-shaped camming surface 1980 adjacent the drive head 1834. The camming surface 1980 frictionally engages a corresponding camming surface 1982 disposed on the adjacent retainer member 1824 shown in FIG. 30 (in a test block for demonstrative purposes with heads 1834 of the cam shafts 1816 hidden) as the cam shaft 1816 is rotated from its undeployed starting position (on left side of FIG. 30), to a partially deployed position, and then to its fully deployed position 180 degrees from its starting position. The camming surfaces 1980 and 1982 are inclined relative to the longitudinal axis 1981 so that as the camming surfaces 1980, 1982 engage and cam against each other, the cam shaft 1816 is shifted axially towards the anterior direction (as installed in the spine).

This frictional interaction between the camming surfaces 1980, 1982 and a biasing force exerted by the retainer members 1824 on the cam shaft 1816 caused by the deformation of the retainer members 1824 provides tactile feedback to the surgeon. The deformation of the retainer members is preferably elastic, such that the retainer members 1824 will return to their original shape when the cam shaft 1816 is in its fully deployed position. Alternatively, the deformation could be plastic, wherein the retainer members 1824 undergo some irreversible deformation. This is acceptable when the securing mechanism is not deployed and retracted repeatedly.

Once the cam shaft 1816 is turned a full 180 degrees, the cam shaft camming surface 1980 snaps into a recess 1984 formed in the adjacent retainer member 1824, due to the biasing force exerted on the cam shaft 1816 by the flexed retainer members 1824. The recess 1984 and cam shaft camming surface 1980 is formed such that the camming surface 1980 becomes trapped in the recess 1984 and blocks derotation of the cam shaft 1816. More specifically, the cam projection 1979 has a straight, trailing edge surface 1983 that is turned toward the straight edge surface 1985 of recess 1984. Once the trailing edge surface 1983 clears the recess surface 1985, the cam surface 1980 will have traveled past the corresponding camming surface 1982 so that the cam surfaces 1980 and 1982 are disengaged from one another. This removes the axial biasing force that their camming engagement generates, so that the cam projection 1979 travels or snaps axially back into the recess 1984. In this orientation, the flat edge surfaces are in confronting relation to each other so that the cam projection 1979 cannot be moved back out of the recess 1984.

Figure 33:
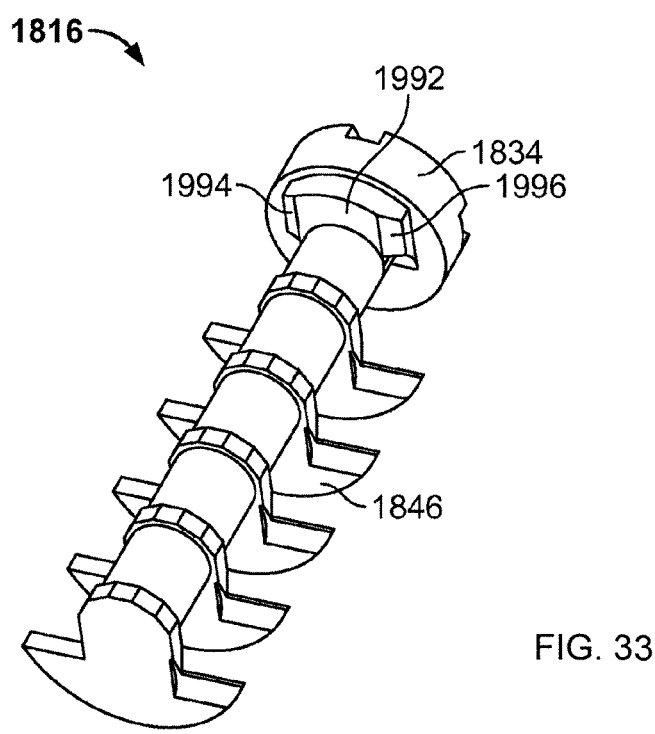
FIG. 33 is a posterolateral perspective view of a cam shaft securing mechanism according to the present invention illustrating a dual chamfered camming surface.
Figure 32:
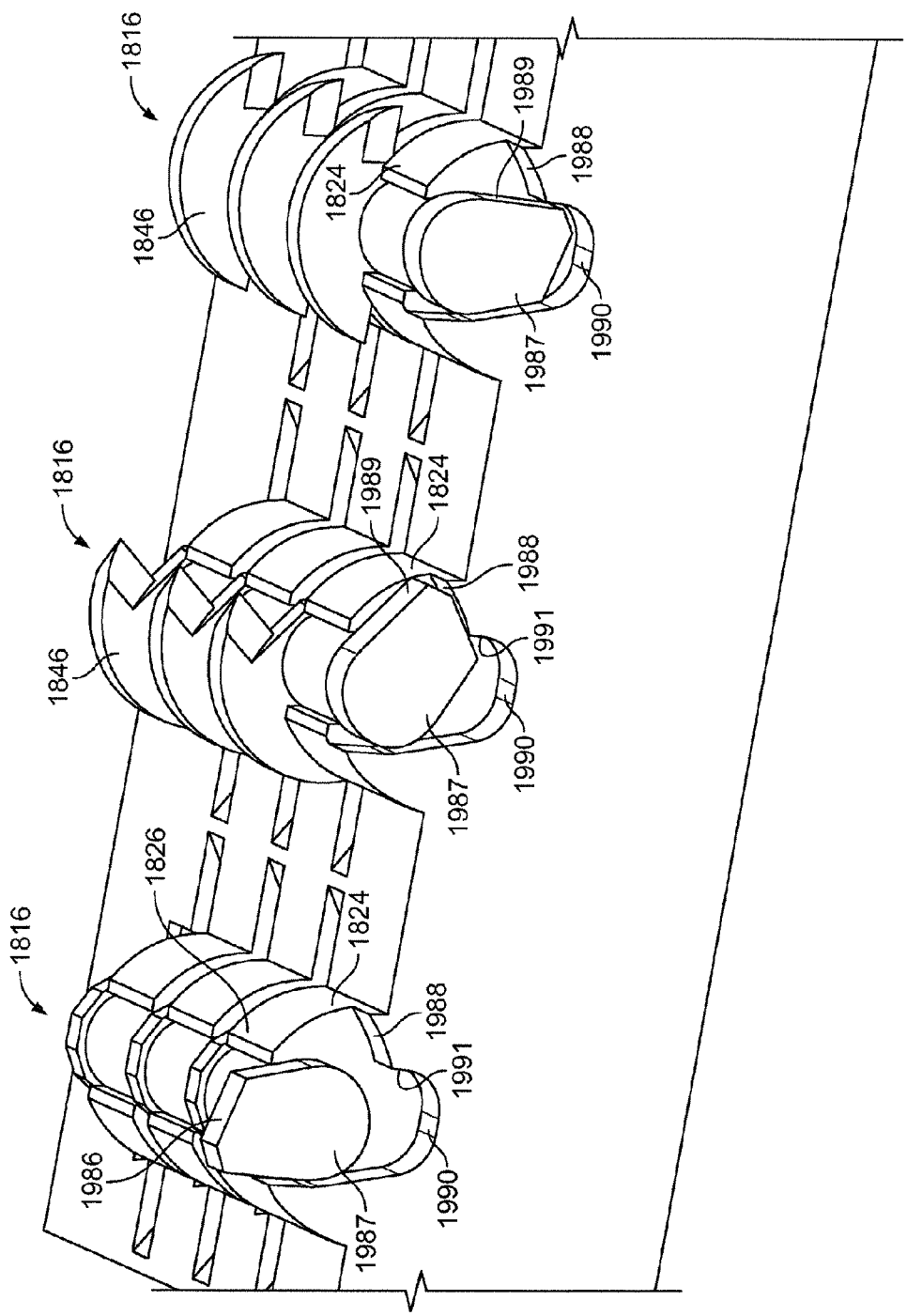
FIG. 32 is an anterolateral perspective view of the cam shaft of FIG. 31 with the head hidden disposed in a test block mimicking a securing mechanism for an implant for illustration of the operation of the cam shaft. The cam shaft is shown in an undeployed position, a partially deployed position, and fully deployed, from left to right.
Figure 35:
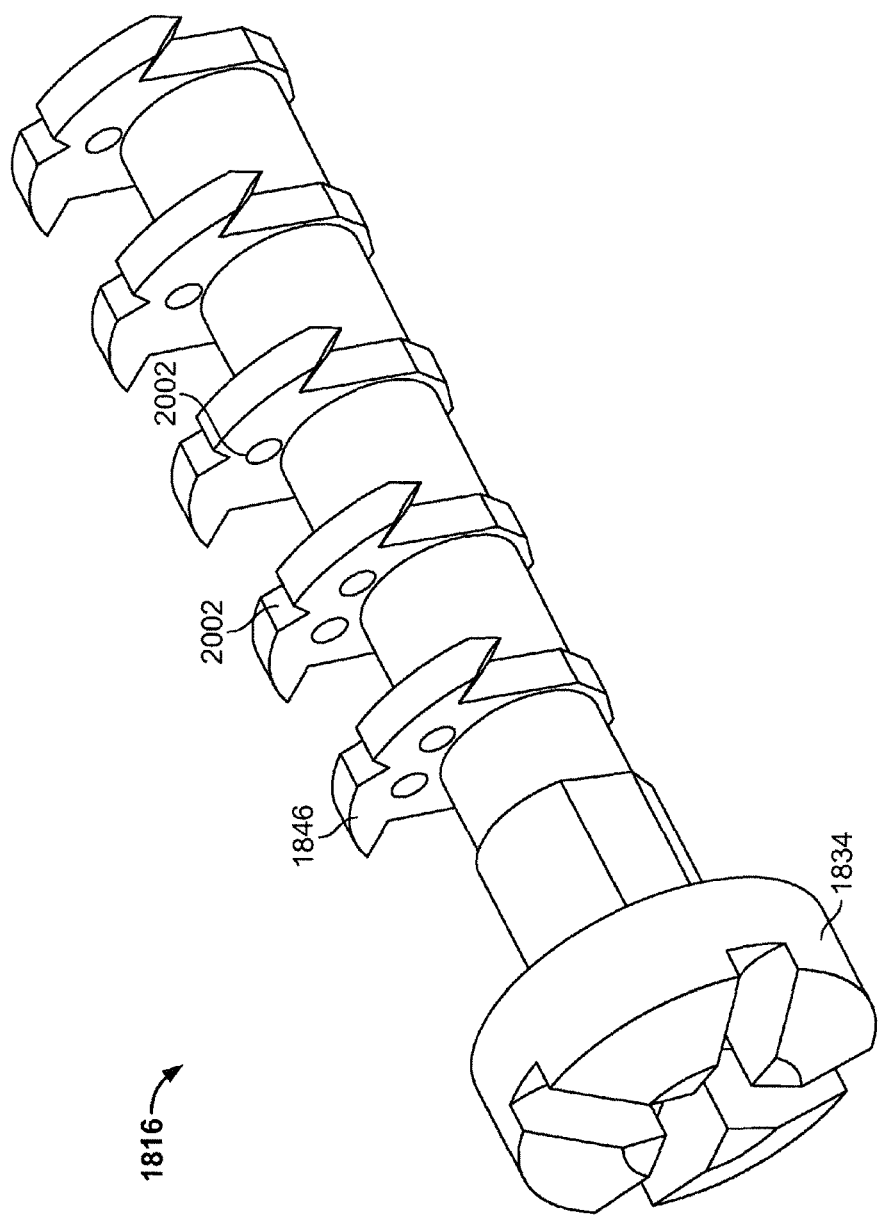
FIG. 35 is an anterolateral perspective view of an alternate embodiment of a cam shaft securing mechanism according to the present invention.

Now referring to FIGS. 33 and 35, another embodiment of the securing mechanism for providing tactile feedback to the surgeon and preventing retraction of the securing mechanism is disclosed. The cam shaft 1816 has a flat camming surface 1986 adjacent the drive head 1834. As shown in FIG. 32 (in a test block arrangement similar to FIG. 30), the flat camming surface 1986 frictionally engages a corresponding camming surface 1988 formed in the adjacent retainer member 1824. The camming surfaces 1986, 1988 operate similarly to the wedge shape camming surface 1980 and corresponding camming surface 1982, except that instead of biasing the cam shaft 1816 axially, they bias the cam shaft 1816 generally vertically. As the cam shaft 1816 is rotated from its starting position to the fully deployed position (at 180 degrees from its undeployed starting position), the flat camming surface 1986 of the cam shaft 1816 engages the corresponding camming surface 1988 of the retainer member 1824. This pushes the cam shaft 1816 generally upward away from the retainer members 1824, which biases the cam shaft 1816 against the upwardly extending arm 1826 of the retaining members 1824, providing tactile feedback to the surgeon in the form of increased resistance to the rotation of the cam shaft 1816 until the shaft is almost turned a full 180 degrees. The resistance dissipates quickly as the camming surfaces begin to disengage each other. In fact, the deformation of the retaining members 1824 may help to propel the cam shaft into a fully deployed position. This propulsion and dissipation of resistance constitutes additional tactile feedback which varies during the deployment of the securing mechanism and informs the surgeon that the cam members 1846 are fully deployed. Once the cam shaft 1816 is turned a full 180 degrees, the flat camming surface 1986 snaps into a recess 1990 formed in the adjacent retainer member 1824, due to the generally vertical biasing force exerted by the flexed retainer members 1824. The recess 1990 and cam shaft camming surface 1986 are formed such that the camming surface 1986 becomes trapped in the recess 1990 and prevents derotation of the cam shaft 1816.

More specifically, the cam projection 1987 has a straight, trailing edge surface 1989 that is turned toward the straight edge surface 1991 of recess 1990. Once the trailing edge surface 1989 clears the recess surface 1991, the cam surface 1986 will have traveled past the corresponding camming surface 1988 so that the cam surfaces 1986 and 1988 are disengaged from one another. This removes the vertical biasing force that their camming engagement generates, so that the cam projection 1987 travels or snaps axially down into the recess 1990. In this orientation, the straight edge surfaces 1989, 1991 are in confronting relation to each other so that the cam projection 1987 cannot be moved back out of the recess 1990.

Figure 34:
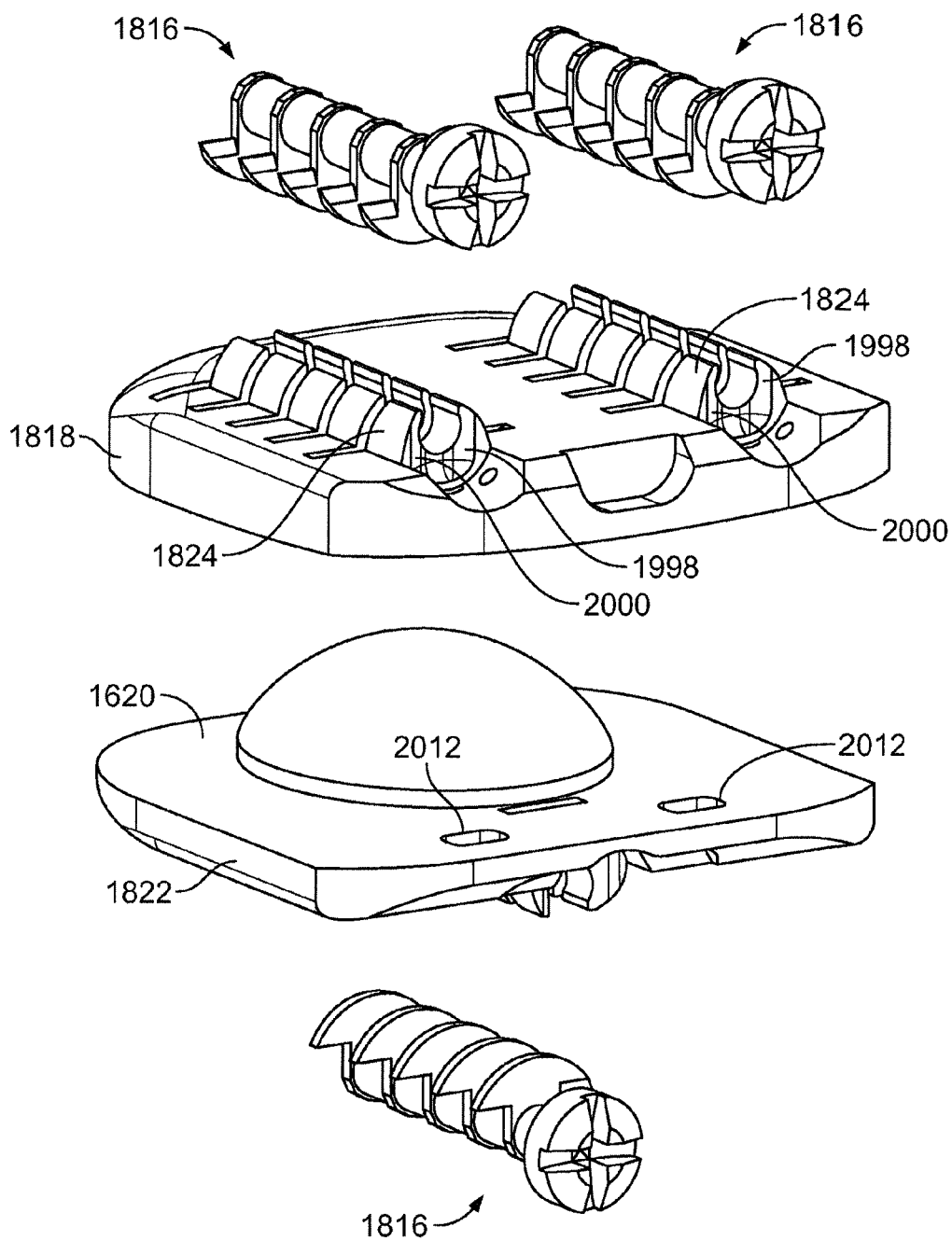
FIG. 34 is an anterolateral exploded view of the artificial disc implant of FIG. 28.

In another form shown in FIGS. 33 and 34, the cam shaft 1816 has a dual chamfered camming surface 1992 for providing tactile feedback to the surgeon and preventing derotation of the cam shaft 1816. In this embodiment, a chamfered surface 1994 for providing resistive feedback during deployment of the cam lobes 1846 is provided on one side of the camming surface 1992, which is engaged when the cam shaft 1816 is rotated in a clockwise direction. Another chamfered surface 1996 is provided on the other side of the camming surface 1992 for providing resistive feedback during retraction of the cam lobes 1846, which is engaged when the cam shaft 1816 is rotated in a counterclockwise direction. Like the embodiments described directly above, the camming surface 1992 engages a corresponding generally concave camming surface 1998 formed in the adjacent retainer member 1824. The corresponding camming surface 1998 is formed such that the chamfered camming surface 1992 adjacent the drive head engages the corresponding camming surface 1998 causing the cam shaft 1816 to bias against the retainer members 1824 and provide tactile or resistive feedback as described above. Unlike the embodiments above, the cam 1816 may be manually retracted by turning the cam shaft 1816 back 180 degrees in the counterclockwise direction. This is desirable if the surgeon wishes to adjust the implant 1752 or prepare the implantation site further. Over-rotation and rotation in the wrong direction is prevented by leaving a raised surface 2000 on the opposite side of the corresponding camming surface 1998 such that it is virtually impossible to turn the cam shaft 1816 in the wrong direction due to interference between the camming surface 1992 on the cam 1816 and the raised surface 2000.

Figure 36:
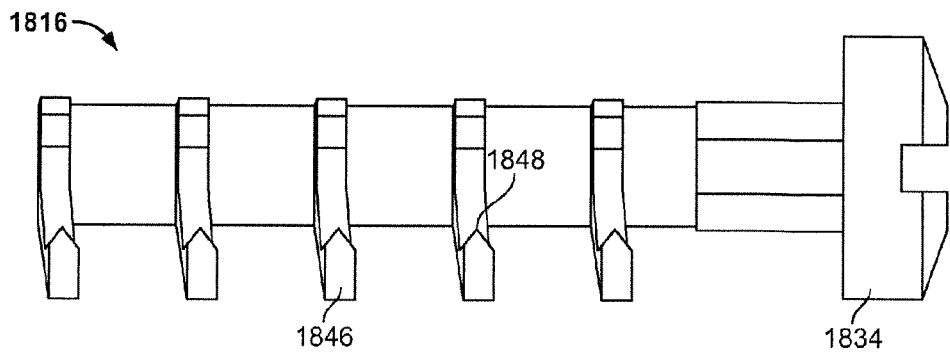
FIG. 36 is a side view of an alternate embodiment of a cam shaft securing mechanism according to the present invention illustrating cupped cam members.
Figure 37:
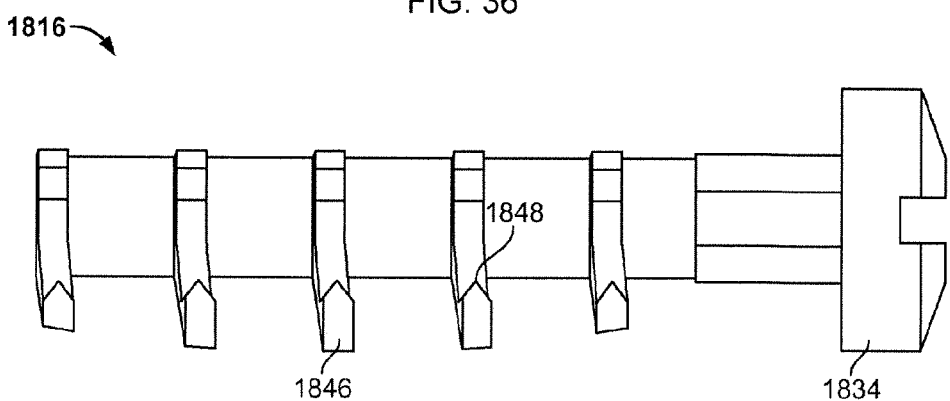
FIG. 37 is a side view of an alternate embodiment of a cam shaft securing mechanism according to the present invention illustrating contoured cam members.
Figure 38:
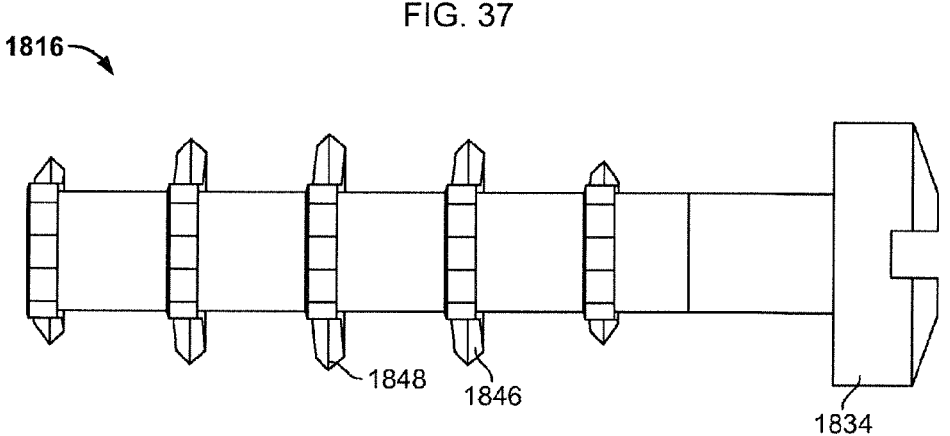
FIG. 38 is a top view of an alternate embodiment of a cam shaft securing mechanism according to the present invention illustrating contoured cam members.
Figure 40:
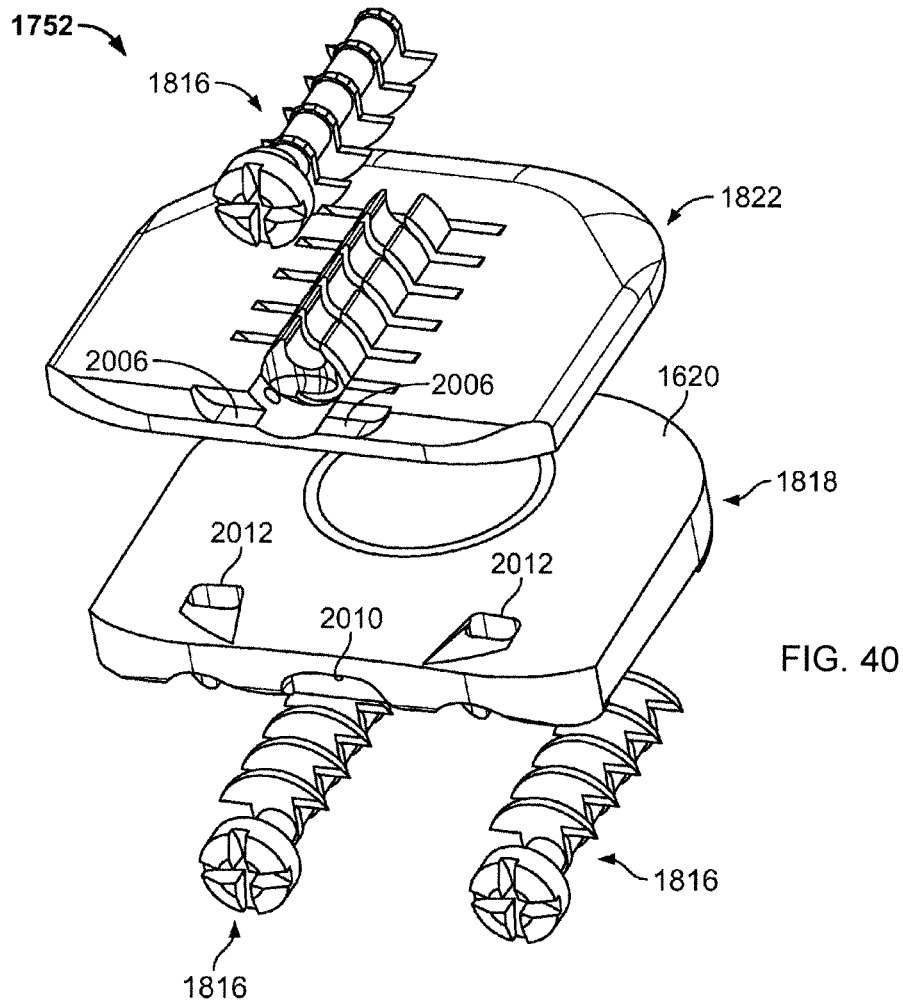
FIG. 40 is an inverted anterolateral exploded view of the artificial disc implant of FIG. 26.

The cam shafts 1816, cam members, lobes, or fins 1846 may take on different geometries and orientations to improve performance of the securing mechanism. For example, the camming fins may include serrations 2002, as shown in FIG. 35, divots, or recesses 2002 to promote boney ingrowth. The serrations 2002 may also help to cut the bone when the cam 1816 is rotated. In addition, the camming fins 1846 may be cupped or slanted, as shown in FIG. 36, to further promote anchoring of the implant 1752 to the vertebrae. In a preferred embodiment, the camming fins 1846 are cupped about 8 degrees. Further, as shown in FIGS. 37 and 38, the camming fins 1846 may have an outside contour, such that shape or size of the cam fins 1846 varies from one end of the cam shaft 1816 to the other. The contour may match the profile of the endplates to take advantage of the softer bone in the center of the vertebrae as opposed to the harder-denser bone at the periphery of the vertebrae. Further, the cam shafts 1816 may have any number of cam members 1846. In a preferred embodiment, each cam shaft 1816 may have between three and five cam members 1846. Larger implants may have five members 1846 per cam shaft 1816, while smaller implants may have only three. The cam shafts 1816 are preferably made from titanium or stainless steel, and may be coated with a bone-growth promoting substance, such as hydroxyapatite, tricalcium phosphates, or calcium phosphates.

Cam members 1846 that cut or imbed themselves into the bone provide advantages over other securing mechanisms. For instance, securing mechanisms that use static projections such as spikes and keels may rely on the subsidence of the bone around the securing mechanism to secure the implant. Static securing mechanisms are less desirable because they may not properly secure the implant to the bone until the bone begins to subside around the securing mechanism, thus, the implant may tend to migrate prior to bone subsidence. However, dynamic securing mechanisms like cam members 1846 with cutting surfaces 1848 actively cut into or imbed themselves into the bone, instead of relying on the subsidence of the bone. In this manner, dynamic securing mechanisms create a much more reliable and stable connection between the implant 1752 and the vertebra. These benefits translate into a more robust and reliable implant 1752, which means quicker recovery times and increased mobility for the patient.

Figure 39:
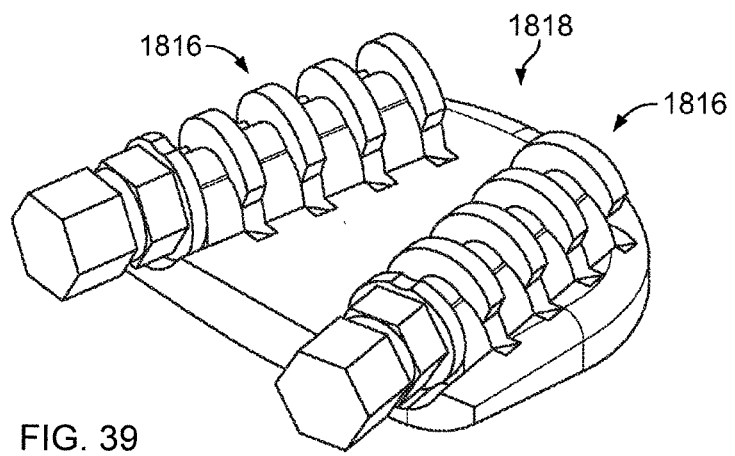
FIG. 39 is an anterolateral perspective view of an alternate embodiment of the artificial disc implant according to the present invention.

In another form, the cam shafts 1816 on the upper disc implant member 1818 may be disposed at converging or diverging angles, such as shown in FIG. 39. This orientation prevents migration of the implant 1752 not only in an anterior/posterior direction, but also substantially in the lateral direction as well. Naturally, the lower disc implant member 1822 may employ such a configuration.

It should be noted that the cam shafts 1816 provide certain advantages over other securing mechanisms, such as screws. For instance, screws do not provide a significant level of tactile feedback. It is very difficult for a surgeon to determine how far a screw has been turned, and therefore he may over- or under-rotate the screw, increasing the risk of implant migration and failure. In addition, metal screws may damage the implant if over-tightened. If the implant is made of a relatively soft material, such as PEEK, the metal screws will easily strip and damage the implant if over-tightened. Moreover, a surgeon is more likely to over-tighten a screw housed within a polymer because the screw is so much harder than the polymer that he will not be able to feel when the screw has been over-tightened. To alleviate this problem, the implant 1752 may be fabricated with a metal portion for housing the screw combined with a polymer, but this greatly increases the difficulty in manufacturing the implant 1752, as well as its cost, and is therefore less desirable. In addition, over-rotation of a screw may advance the screw beyond its intended range of motion, and may cause it to protrude from the implant and cause damage to vital areas in and around the spine. Because the cams do not advance or retreat as they are rotated, there is no danger that the cams 1846 will be accidentally projected into other vital areas.

The articulating joint surfaces are preferably a combination of PEEK articulating on PEEK, PEEK on carbon reinforced (CR) PEEK, or CR PEEK on CR PEEK. Boney integration of these implants may benefit from prepared osteoconductive surfaces or coatings described elsewhere in this document.

It is preferable that the radiolucent implant includes one or more small radiopaque markers which will show on up an X-ray image to assist the surgeon in positioning the implant during surgery. The preferred material for these markers is tantalum. Typically these markers will be encased in predetermined locations in the implant at their periphery. Coatings which show up on imaging as a subtle outline of the implant device may also be used.

It is also preferable that the implants disclosed herein include a layer of osteo-conductive or osteo-inductive surfaces or coatings on those implant surfaces in contact with bone or tissue that will assist in securing the implant in a predetermined location. Typically this will occur through boney integration of the bone with the coating or implant surface. Examples of such coatings are hydroxyapatite, calcium phosphates such as tricalcium phosphate, or porous titanium spray.

The implant devices disclosed herein are particularly suited as intervertebral disc replacements for all or a portion of the natural intervertebral disc. In addition, the securing members disclosed herein are also suited for other spinal implants, such as vertebral body replacements, spinal cages, and other fusion promoting implants, as well as other known motion preserving implants. The devices have minimal structural parts and are preferably manufactured from specialized materials that are substantially radiolucent such as PEEK or Carbon-Fiber PEEK in both their structural and joint articulating portions.

Generally, the various systems and methods described herein allow for an implant, such as an artificial disc, to be properly sized, implanted and secured in an intervertebral space with the disc having a bearing interface that preserves motion between the upper and lower vertebrae between which the disc is implanted and secured. In each form described herein, a trial spacer is not only used to assess the size of the intervertebral space so that an appropriately sized disc implant can be selected, it may also be used to assist in generating features in the vertebrae and/or end plates thereof for a securing member that holds and retains the disc implant in the intervertebral space.

In other forms of the invention, the implant may comprise a pharmacological agent used for treating various spinal conditions, including degenerative disc disease, spinal arthritis, spinal infection, spinal tumor and osteoporosis. Such agents include antibiotics, analgesics, anti-inflammatory drugs, including steroids, and combinations thereof. Other such agents are well known to the skilled artisan. These agents are also used in therapeutically effective amounts. Such amounts may be determined by the skilled artisan depending on the specific case.

The pharmacological agents, if any, are preferably dispersed within the implant for in vivo release. The pharmacological agents may be dispersed in the spacer by adding the agents to the implant when it is formed, by soaking a formed implant in an appropriate solution containing the agent, or by other appropriate methods known to the skilled artisan. In other forms of the invention, the pharmacological agents may be chemically or otherwise associated with the implant. For example, the agents may be chemically attached to the outer surface of the implant.

Although the securing members and insertion tools have been described with reference to a disc replacement implant, the securing members and tools may be easily adapted for use with other artificial implants, such as fusion promoting implants, including vertebral body replacements, spinal cages, and the like. In addition, the invention described herein may also be applied to other motion preserving implants, such as those with articulating surfaces, including nucleus replacement implants. Moreover, the securing members, insertion tools, and methods described herein may be implemented in other weight-bearing joint implants, such as ankle, knee, or hip joint implants.

While the invention has been described with respect to specific examples including presently preferred modes of carrying out the invention, those skilled in the art will appreciate that there are numerous variations and permutations of the above described systems and techniques that fall within the spirit and scope of the invention as set forth in the claims.

What is claimed is:

1. An intervertebral disc implant, comprising:
an upper bearing member having a body and an outer bearing surface;
a lower bearing member having a body and an outer bearing surface;
an articulation interface between the upper and lower bearing members for allowing relative movement therebetween;
a securing member disposed on one of the bearing members having an elongate shaft member having a longitudinal axis and a bone-engaging member formed on the shaft member wherein the elongate shaft member and the bone-engaging member are configured to be rotated about the longitudinal axis of the elongate shaft member, wherein the bone-engaging member has a plate-like body extending transversely from the shaft member, the plate-like body having opposite main surfaces having a thickness therebetween and a maximum lateral width thereacross that is greater than the thickness, the plate-like body further including an outer peripheral edge extending about the main surfaces, with the main surfaces tapering down to an elongate cutting edge portion formed along the plate-like body peripheral edge with the cutting edge portion extending radially outwardly from the elongate shaft member, the plate-like body having an undeployed position with the radially extending cutting edge portion facing an adjacent bone so that turning the elongate shaft member toward a deployed position causes the cutting edge portion to cut into and lead the plate-like body into the adjacent bone.

2. The intervertebral disc implant of claim 1, wherein the securing member is entirely disposed within the body of the one bearing member when the bone-engaging member is oriented in the undeployed position.

3. The intervertebral disc implant of claim 1, wherein the elongate shaft member is disposed within a channel disposed on the bearing member.

4. The intervertebral disc implant of claim 1, wherein the securing member comprises a plurality of bone-engaging members.

5. The intervertebral disc implant of claim 4, wherein each of the plurality of bone-engaging members comprise plate-like bodies oriented transversely to the elongate shaft member.

6. The intervertebral disc implant of claim 5, wherein each of the plate-like bodies have elongate cutting edge portions for easing insertion of the plate-like bodies into the adjacent vertebral bone during deployment thereof.

7. The intervertebral disc implant of claim 1, wherein the securing member is connected to the body of the one bearing member via a securing member receiving portion disposed on the implant body having opposing inner surfaces spaced from each other for receiving the elongate shaft member.

8. The intervertebral disc implant of claim 7, wherein the elongate shaft member is received between the opposing inner surfaces by a friction fit.

9. The intervertebral disc implant of claim 1, wherein the upper and lower bearing members are sized and configured to fit entirely between inner surfaces of adjacent vertebrae when the securing member is in the undeployed configuration.

10. The intervertebral disc implant of claim 1, wherein the one bearing member and the securing member disposed thereon are configured such that in the undeployed position, the bone-engaging member extends from the elongate shaft member toward the other bearing member and away from the adjacent bone, such that the securing member shaft is rotated one half rotation to shift the bone-engaging member from the undeployed position to the deployed position.

11. An intervertebral disc implant for being implanted within a vertebral disc joint between adjacent vertebrae, comprising:
an implant body;
a deployable securing member;
a plate-like head portion of the deployable securing member having opposite side surfaces and an outer peripheral cutting edge configured for cutting into a bone, the opposite side surfaces each having a planar configuration;

an actuator engagement portion of the securing member mounted to the implant body to be retained against shifting along the implant body; and an actuator having an elongate body for insertion along the implant body along an insertion axis for deploying the deployable securing member along a deployment axis transverse to the insertion axis, the actuator configured and sized to be retained by the implant body after insertion of the actuator and deployment of the securing member;

the deployable securing member being deployable from an undeployed position, wherein the head portion is remote from an adjacent vertebra, to a deployed position, wherein the deployable securing member is thereby shifted along the deployment axis so that the head portion extends from the implant body for cutting into the adjacent vertebra when the actuator is inserted along the insertion axis so that the actuator body rampingly engages the actuator engagement portion;

the deployable securing member being linearly deployable along the deployment axis via the ramping engagement of the actuator with the actuator engagement portion of the deployable securing member when the actuator is inserted along the insertion axis;

the head portion of the deployable securing member being oriented to be aligned with the actuator engagement portion along the deployment axis and the insertion axis being transverse to the planar side surfaces so that upon deployment the side surfaces resist shifting of the implant body along the insertion axis.

12. The intervertebral disc implant of claim 11, wherein the implant body has an outer bone-engaging surface for non-invasive contact with an inner surface of the adjacent vertebra and a securing member receiving portion of the implant body for mating with the securing member which protrudes outwardly beyond the outer bone-engaging surface.

13. The intervertebral disc implant of claim 12, wherein the securing member receiving portion comprises an elongate opening disposed transversely to the insertion axis for receiving the head portion and allowing the head portion to travel from the undeployed position, wherein the head portion is disposed within the opening, to the deployed position, wherein the head portion protrudes from the opening for engagement with the adjacent vertebra.

14. The intervertebral disc implant of claim 11, wherein the implant body comprises upper and lower bearing members and the implant further comprises:

upper and lower inner arcuate bearing surfaces of the upper and lower bearing members that slidingly engage one another to provide a sliding interface between the upper and lower bearing members that allows the bearing members to articulate with respect to one another.

15. The intervertebral disc implant of claim 14, wherein the upper and lower inner arcuate bearing surfaces are sized and configured to allow the upper and lower bearing members to rotate with respect to one another over a range greater than 13 degrees in both flexion and extension of the vertebral disc joint.

16. The intervertebral disc implant of claim 11, wherein the edge of the head portion is deployed rostrally or caudally into engagement with the adjacent vertebra without substantial translation in another direction.

17. An intervertebral implant, the implant comprising:
an implant body;
a securing member receiving portion on the implant body having an opening;
a deformable securing member having proximal and distal ends defining a longitudinal axis for being inserted into the securing member receiving portion;
a bone-engaging portion of the deformable securing member disposed between the proximal and distal ends thereof so as to be spaced therefrom which is movable from an undeployed orientation, wherein the bone-engaging portion extends along the longitudinal axis of the securing member and is remote from an adjacent vertebra, and a deployed orientation, wherein the bone-engaging portion is brought into contact with the adjacent vertebra for securing the implant body to the adjacent vertebra, wherein the deformable securing member has a structurally weakened portion at a predetermined position thereon to promote plastic deformation thereof at the predetermined position to deploy the bone-engaging member at a desired location and the bone-engaging portion is deployed in a direction transverse to the longitudinal axis of the securing member and through the opening via deformation of the securing member.

18. The intervertebral implant of claim 17, further comprising an abutment surface of the implant body for engaging with the securing member to cause deformation of the securing member by compression of the securing member against the abutment surface.

19. The intervertebral implant of claim 18, wherein the bone-engaging portion is a barb member disposed on the deformable securing member.

20. The intervertebral implant of claim 19, wherein the barb member is disposed flush to an outer surface of the securing member prior to deployment of the barb member.

21. The intervertebral implant of claim 17, wherein the opening of the securing member receiving portion is disposed on an outer bearing surface of the implant body which permits the bone-engaging portion to pass through the opening and engage the adjacent vertebra.

22. The intervertebral implant of claim 17, wherein the deformable securing member comprises a plurality of bone-engaging portions.

* * * * *